(12) United States Patent
Dalmau et al.

(10) Patent No.: US 10,962,554 B2
(45) Date of Patent: Mar. 30, 2021

(54) DIAGNOSIS OF A NEUROLOGICAL DISEASE

(71) Applicants: INSTITUT D'INVESTIGACIONES BIOMÈDIQUES AUGUST PI I SUNYER, Barcelona (ES); INSTITUCIÓ CATALANA DE RECERCA I ESTUDIS AVANÇATS, Barcelona (ES); UNIVERSITAT DE BARCELONA, Barcelona (ES); HOSPITAL CLÍNIC DE BARCELONA, Barcelona (ES)

(72) Inventors: Josep Dalmau, Barcelona (ES); Francesc Graus, Barcelona (ES)

(73) Assignees: INSTITUT D'INVESTIGACIONES BIOMÈDIQUES AUGUST PI I SUNYER, Barcelona (ES); INSTITUCIÓ CATALANA DE RECERCA I ESTUDIS AVANÇATS, Barcelona (ES); UNIVERSITÄT DE BARCELONA, Barcelona (ES); HOSPITAL CLÍNIC DE BARCELONA, Barcelona (ES)

( * ) Notice: Subject to any disclaimer, the term of this patent is extended or adjusted under 35 U.S.C. 154(b) by 0 days.

(21) Appl. No.: 16/051,129

(22) Filed: Jul. 31, 2018

(65) Prior Publication Data
US 2018/0335439 A1   Nov. 22, 2018

Related U.S. Application Data

(63) Continuation of application No. 15/116,179, filed as application No. PCT/EP2015/052529 on Feb. 6, 2015, now abandoned.

(30) Foreign Application Priority Data

Feb. 7, 2014   (EP) .................................... 14154384

(51) Int. Cl.
*G01N 33/68*   (2006.01)
*G01N 33/564*  (2006.01)
*C07K 16/28*   (2006.01)

(52) U.S. Cl.
CPC ..... *G01N 33/6896* (2013.01); *C07K 16/2803* (2013.01); *G01N 33/564* (2013.01); *G01N 33/6854* (2013.01); *G01N 2800/2814* (2013.01); *G01N 2800/2821* (2013.01); *G01N 2800/2864* (2013.01)

(58) Field of Classification Search
None
See application file for complete search history.

(56) References Cited

U.S. PATENT DOCUMENTS

| 2006/0003323 A1* | 1/2006 | Alsobrook | C07K 14/47 435/6.14 |
|---|---|---|---|
| 2012/0263764 A1 | 10/2012 | Watson | |
| 2016/0349275 A1 | 12/2016 | Dalmau et al. | |

FOREIGN PATENT DOCUMENTS

| WO | 2002074906 | | 9/2002 |
|---|---|---|---|
| WO | WO 2002/072794 | * | 9/2002 |
| WO | WO 2002/074906 | * | 9/2002 |

OTHER PUBLICATIONS

Black, et al., "Advances in the Design and Delivery of Peptide Subunit Vaccines with a Focus on Toll-Like Receptor Agonists", Expert Review of Vaccines, vol. 9, No. 2, Feb. 1, 2010, pp. 157-173, XP055164967, ISSN: 1476-0584.
Jackson, et al., "Preparation and Properties of Totally Synthetic Immunogens", Vaccine, Elsevier, Amsterdam, NL, vol. 18, No. 3-4, Sep. 1, 1999, pp. 355-361, XP002624403, ISSN:0264-410X.
Moreau, et al., "Computational Design of Immunogenic Peptides", BMC Bioinformatics, Biomed Central, London, GB, vol. 9, No. 1, Jan. 30, 2008, p. 71, XP021031953, ISSN: 1471-2105.
Simon, et al., "Passage, Clinical Neurology", Clinical Neurology, Jan. 1, 2009, Lange Medical Books/McGraw-Hill, US, XP55578837, ISBN: 978-0-07-154644-7, p. 43.
Amendment and Response to the Final Office Action dated Jan. 4, 2018 for U.S. Appl. No. 15/116,179.
Amendment and Response to the Non-Final Office Action dated Jul. 13, 2017 for U.S. Appl. No. 15/116,179.

(Continued)

*Primary Examiner* — Adam Weidner
(74) *Attorney, Agent, or Firm* — Stoel Rives LLP; Kelly A. Echols

(57) ABSTRACT

The present invention concerns subject matter connected to or making use of IgLON5, IgLON5 fragments and variants of IgLON5 and IgLON5-fragments. In particular the present invention relates to a use of a polypeptide comprising one or more sequences of IgLON5, an IgLON5-fragment or a variant thereof for the diagnosis of a disease, in vitro methods for diagnosing such a disease, a polypeptide comprising one or more sequences of IgLON5, an IgLON5-fragment or a variant thereof or a nucleic acid encoding said polypeptide for use in the treatment of a disease, a pharmaceutical composition comprising such polypeptide, a method for treating such a disease, an autoantibody binding to IgLON5, an IgLON5-fragment or a variant thereof, a method for isolating such autoantibody, a medical or diagnostic device comprising such autoantibody or such polypeptide and a test kit for the diagnosis of a disease, which test kit comprises such autoantibody and/or such polypeptide.

4 Claims, 8 Drawing Sheets
Specification includes a Sequence Listing.

(56) References Cited

OTHER PUBLICATIONS

European Search Report dated Apr. 8, 2014 for EP application 14154384.3.
International Search Report dated Aug. 13, 2015 for international application PCT/EP2015/052529.
Non-Final Office Action dated Apr. 27, 2018 for U.S. Appl. No. 15/116,179.
IGLON5 Gene—GeneCards: IGLO5 Protein: IGLO5 Antibody, GeneCards Human Gene Database, Mar. 31, 2014, XP055111080, retrieved from the Internet: URL: http://www.genecards.org/cgi-bin/carddisp.p;?genge+IGLON5.
NTM Gene—GeneCards: NTRI Protein: NTRI Antibody, GeneCards Human Gene Database, Mar. 31, 2014, XP055111081, retrieved from the Internet: URL: http://www.genecards.org/cgi-bin/carddisp.pl?gene=NTM&search=ntm#diseases.
Final Office Action dated Oct. 11, 2017 for U.S. Appl. No. 15/116,179.
Non-Final Office Action dated Mar. 17, 2017 for U.S. Appl. No. 15/116,179.
Hoftberger, et al.,"Clinical Neuropathology Practice Guide May 2012: Updated Guideline for the Diagnosis of Anti-Neuronal Antibodies", Clinical Neuropathology, vol. 31—No. May 2012 (pp. 337-341).
Leypoldt, et al.,"Autoimmune Encephalopathies", Annals of the New York Academy of Sciences, vol. 1338, No. 1, Oct. 14, 2014 (pp. 94-114).
Petit-Pedrol, et al.,"Encephalitis with Refractory Seizures, Status Epilepticus, and Antibodies to the GABAA Receptor: A Case Series, Characterisation of the Antigen, and Analysis of the Effects of Antibodies", Lancet Neurology, Lancet Publishing Group, London, GB, vol. 13, No. 3, Jan. 22, 2014 (pp. 276-286).
Sabater, et al.,"A Novel Non-Rapid-Eye Movement and Rapid-Eye-Movement Parasomnia with Sleep Breething Disorder Associated with Antibodies to IgLON5: A Case Series, Charaterisation of the Antigen, and Post-Mortem Study", The Lancet Neurology, vol. 13, No. 6, Apr. 3, 2014 (pp. 575-586).
Chinese Office Action dated Jul. 24, 2019 for CN application 201580029012.5.
CN Office action dated Nov. 28, 2019 for CN appliction 201580002912.5.
European Office Action dated Mar. 4, 2020 for EP application 15702809.3.
Chinese Office Action dated May 6, 2020.
European Patent Application intention to grant dated Jun. 23, 2020.

* cited by examiner

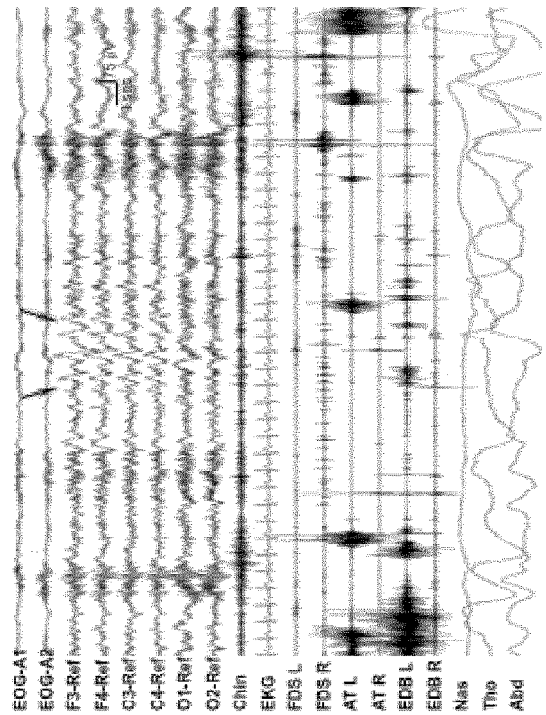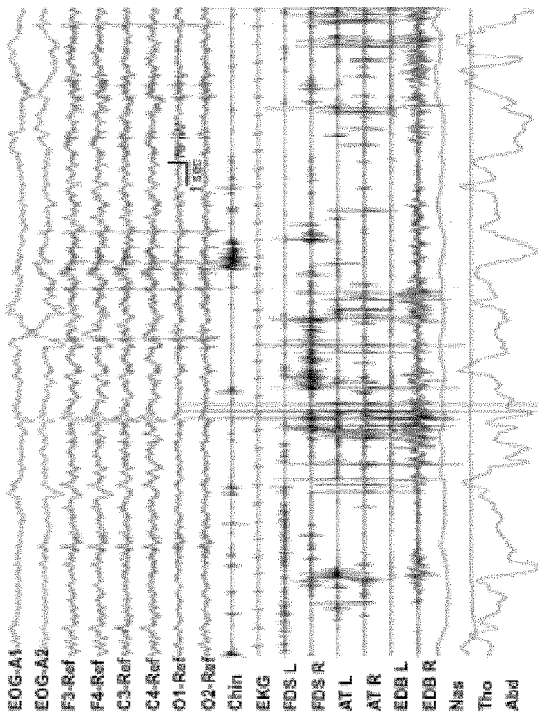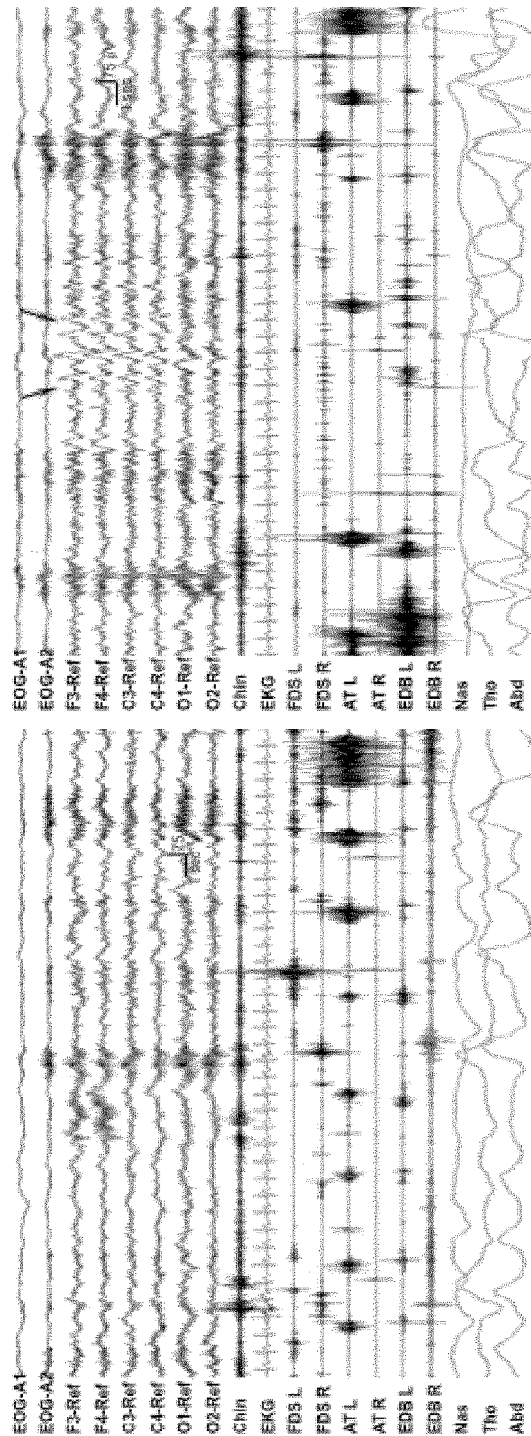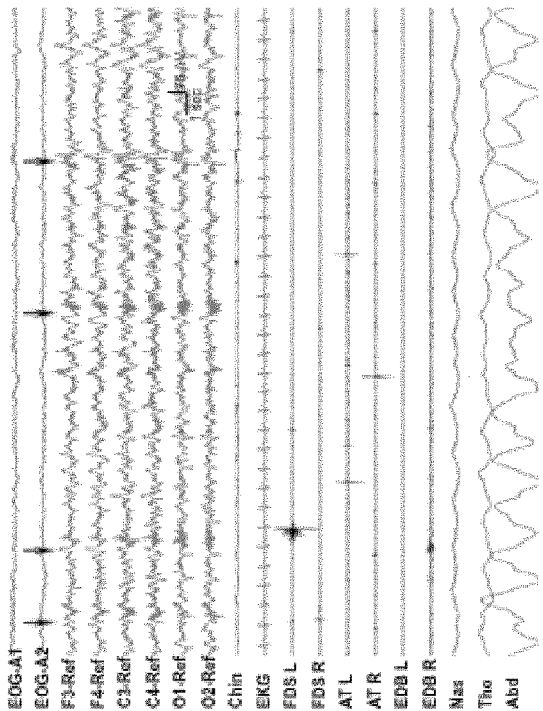
Fig.2

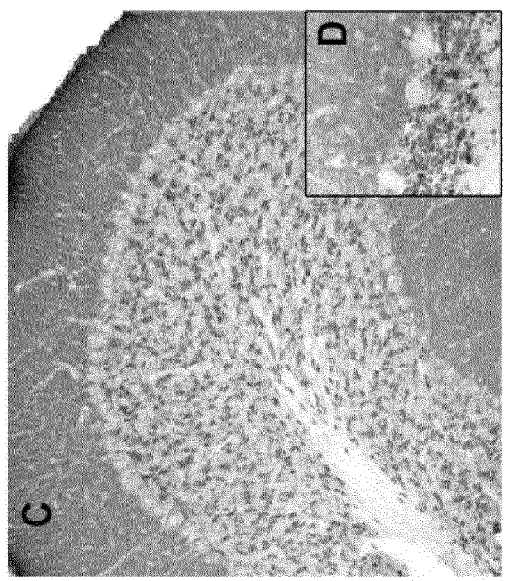
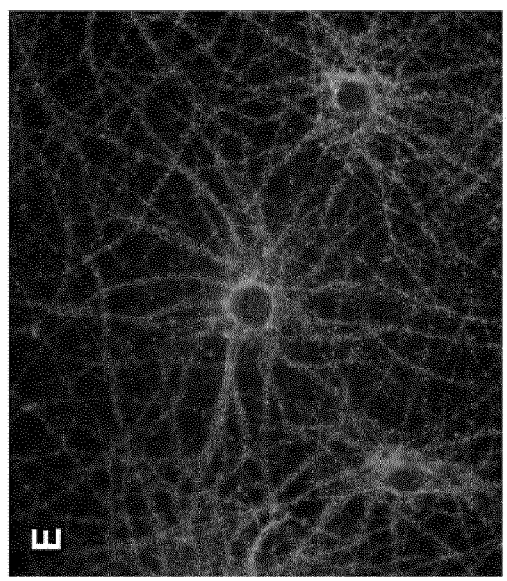
Fig.3

A) MASS SPECTROMETRY EXPERIMENT 1

| Protein name | Peptide sequence | Best Peptide identification probability | Best SEQUEST XCorr score | Best SEQUEST DCn score |
|---|---|---|---|---|
| IgLON family member 5 | GQAGEYECVTHNGVNSAPDSRR (SEQ ID NO:2) | 95.00% | 5.08 | 0.0241 |
| IgLON family member 5 | LLSSGSAEGLK (SEQ ID NO:11) | 95.00% | 2.79 | 0.29 |
| IgLON family member 5 | SNILYAGNDRWTSDPR (SEQ ID NO:4) | 95.00% | 2.84 | 0.417 |

```
MDAYFTECIP SKTNKRYFYN VCVTALAGLA VISRGLLSQS LEFSSPADNY TVCEGDNATL SCFIDEHVTR
VAWLNRSNIL YAGNDRWTSD PRVRLLINTP EEFSILITQV GLGDEGLYTC SFQTRHQPYT TQVYLIVHVP
ARIVNISSPV AVNEGGNVNL LCLAVGRPEP TVTWRQLRDG FTSEGEILEI SDIQRGQAGE YECVTHNGVN
SAPDSRRVLV TVNYPPTITD VTSARTALGR AALLRCEAMA VPPADFQWYK DDRLLSSGSA EGLKVQTERT
RSMLLFANVS ARHYGNYTCR AANRLGASSA SMRLLRPGSL ENSAPRPPGP LTLLSALSWL WWRM
 (SEQ ID NO:12)
```

B) MASS SPECTROMETRY EXPERIMENT 2

| Protein name | Peptide sequence | Best Peptide identification probability | Best SEQUEST XCorr score | Best SEQUEST DCn score |
|---|---|---|---|---|
| IgLON family member 5 | DGFTSEGEILEISDIQR (SEQ ID NO:5) | 95.00% | 5.31 | 0.469 |
| IgLON family member 5 | GQAGEYECVTHNGVNSAPDSR (SEQ ID NO:6) | 95.00% | 4.36 | 0.0618 |
| IgLON family member 5 | HQPYTTQVYLIVHVPAR (SEQ ID NO:7) | 95.00% | 2.83 | 0.45 |
| IgLON family member 5 | SMLLFANVSAR (SEQ ID NO:8) | 95.00% | 3.94 | 0.465 |
| IgLON family member 5 | SNILYAGNDR (SEQ ID NO:9) | 95.00% | 3.26 | 0.374 |
| IgLON family member 5 | SNILYAGNDRWTSDPR (SEQ ID NO:4) | 95.00% | 4.34 | 0.494 |
| IgLON family member 5 | VLVTVNYPPTITDVTSAR (SEQ ID NO:10) | 95.00% | 4.46 | 0.562 |

```
MDAYFTECIP SKTNKRYFYN VCVTALAGLA VISRGLLSQS LEFSSPADNY TVCEGDNATL SCFIDEHVTR
VAWLNRSNIL YAGNDRWTSD PRVRLLINTP EEFSILITQV GLGDEGLYTC SFQTRHQPYT TQVYLIVHVP
ARIVNISSPV AVNEGGNVNL LCLAVGRPEP TVTWRQLRDG FTSEGEILEI SDIQRGQAGE YECVTHNGVN
SAPDSRRVLV TVNYPPTITD VTSARTALGR AALLRCEAMA VPPADFQWYK DDRLLSSGSA EGLKVQTERT
RSMLLFANVS ARHYGNYTCR AANRLGASSA SMRLLRPGSL ENSAPRPPGP LTLLSALSWL WWRM
 (SEQ ID NO:12)
```

Fig. 7

SEQUENCE LISTING

```
<160> NUMBER OF SEQ ID NOS: 12

<210> SEQ ID NO 1
<211> LENGTH: 336
<212> TYPE: PRT
<213> ORGANISM: human

<400> SEQUENCE: 1

Met Pro Pro Pro Ala Pro Gly Ala Arg Leu Arg Leu Leu Ala Ala Ala
1               5                   10                  15

Ala Leu Ala Gly Leu Ala Val Ile Ser Arg Gly Leu Leu Ser Gln Ser
                20                  25                  30

Leu Glu Phe Asn Ser Pro Ala Asp Asn Tyr Thr Val Cys Glu Gly Asp
            35                  40                  45

Asn Ala Thr Leu Ser Cys Phe Ile Asp Glu His Val Thr Arg Val Ala
        50                  55                  60

Trp Leu Asn Arg Ser Asn Ile Leu Tyr Ala Gly Asn Asp Arg Trp Thr
65                  70                  75                  80

Ser Asp Pro Arg Val Arg Leu Leu Ile Asn Thr Pro Glu Glu Phe Ser
                85                  90                  95

Ile Leu Ile Thr Glu Val Gly Leu Gly Asp Glu Gly Leu Tyr Thr Cys
```

```
                100                 105                 110
Ser Phe Gln Thr Arg His Gln Pro Tyr Thr Thr Gln Val Tyr Leu Ile
            115                 120                 125
Val His Val Pro Ala Arg Ile Val Asn Ile Ser Ser Pro Val Thr Val
            130                 135                 140
Asn Glu Gly Gly Asn Val Asn Leu Leu Cys Leu Ala Val Gly Arg Pro
145                 150                 155                 160
Glu Pro Thr Val Thr Trp Arg Gln Leu Arg Asp Gly Phe Thr Ser Glu
                165                 170                 175
Gly Glu Ile Leu Glu Ile Ser Asp Ile Gln Arg Gly Gln Ala Gly Glu
            180                 185                 190
Tyr Glu Cys Val Thr His Asn Gly Val Asn Ser Ala Pro Asp Ser Arg
            195                 200                 205
Arg Val Leu Val Thr Val Asn Tyr Pro Pro Thr Ile Thr Asp Val Thr
            210                 215                 220
Ser Ala Arg Thr Ala Leu Gly Arg Ala Ala Leu Leu Arg Cys Glu Ala
225                 230                 235                 240
Met Ala Val Pro Pro Ala Asp Phe Gln Trp Tyr Lys Asp Asp Arg Leu
                245                 250                 255
Leu Ser Ser Gly Thr Ala Glu Gly Leu Lys Val Gln Thr Glu Arg Thr
            260                 265                 270
Arg Ser Met Leu Leu Phe Ala Asn Val Ser Ala Arg His Tyr Gly Asn
            275                 280                 285
Tyr Thr Cys Arg Ala Ala Asn Arg Leu Gly Ala Ser Ser Ala Ser Met
            290                 295                 300
Arg Leu Leu Arg Pro Gly Ser Leu Glu Asn Ser Ala Pro Arg Pro Pro
305                 310                 315                 320
Gly Leu Leu Ala Leu Leu Ser Ala Leu Gly Trp Leu Trp Trp Arg Met
                325                 330                 335

<210> SEQ ID NO 2
<211> LENGTH: 22
<212> TYPE: PRT
<213> ORGANISM: artificial
<220> FEATURE:
<223> OTHER INFORMATION: rodent/human IgLON5fragment

<400> SEQUENCE: 2

Gly Gln Ala Gly Glu Tyr Glu Cys Val Thr His Asn Gly Val Asn Ser
1               5                   10                  15

Ala Pro Asp Ser Arg Arg
            20

<210> SEQ ID NO 3
<211> LENGTH: 11
<212> TYPE: PRT
<213> ORGANISM: artificial
<220> FEATURE:
<223> OTHER INFORMATION: human IgLON5 fragment

<400> SEQUENCE: 3

Leu Leu Ser Ser Gly Thr Ala Glu Gly Leu Lys
1               5                   10

<210> SEQ ID NO 4
<211> LENGTH: 16
<212> TYPE: PRT
<213> ORGANISM: artificial
<220> FEATURE:
```

```
<223> OTHER INFORMATION: rodent/human IgLON5 fragment

<400> SEQUENCE: 4

Ser Asn Ile Leu Tyr Ala Gly Asn Asp Arg Trp Thr Ser Asp Pro Arg
1               5                   10                  15

<210> SEQ ID NO 5
<211> LENGTH: 17
<212> TYPE: PRT
<213> ORGANISM: artificial
<220> FEATURE:
<223> OTHER INFORMATION: rodent/human IgLON5 fragment

<400> SEQUENCE: 5

Asp Gly Phe Thr Ser Glu Gly Glu Ile Leu Glu Ile Ser Asp Ile Gln
1               5                   10                  15

Arg

<210> SEQ ID NO 6
<211> LENGTH: 21
<212> TYPE: PRT
<213> ORGANISM: artificial
<220> FEATURE:
<223> OTHER INFORMATION: rodent/human IgLON5 fragment

<400> SEQUENCE: 6

Gly Gln Ala Gly Glu Tyr Glu Cys Val Thr His Asn Gly Val Asn Ser
1               5                   10                  15

Ala Pro Asp Ser Arg
            20

<210> SEQ ID NO 7
<211> LENGTH: 17
<212> TYPE: PRT
<213> ORGANISM: artificial
<220> FEATURE:
<223> OTHER INFORMATION: rodent/human IgLON5 fragment

<400> SEQUENCE: 7

His Gln Pro Tyr Thr Thr Gln Val Tyr Leu Ile Val His Val Pro Ala
1               5                   10                  15

Arg

<210> SEQ ID NO 8
<211> LENGTH: 11
<212> TYPE: PRT
<213> ORGANISM: artificial
<220> FEATURE:
<223> OTHER INFORMATION: rodent/human IgLON5 fragment

<400> SEQUENCE: 8

Ser Met Leu Leu Phe Ala Asn Val Ser Ala Arg
1               5                   10

<210> SEQ ID NO 9
<211> LENGTH: 10
<212> TYPE: PRT
<213> ORGANISM: artificial
<220> FEATURE:
<223> OTHER INFORMATION: rodent/human IgLON5 fragment

<400> SEQUENCE: 9

Ser Asn Ile Leu Tyr Ala Gly Asn Asp Arg
1               5                   10
```

<210> SEQ ID NO 10
<211> LENGTH: 18
<212> TYPE: PRT
<213> ORGANISM: artificial
<220> FEATURE:
<223> OTHER INFORMATION: rodent/human IgLON5 fragment

<400> SEQUENCE: 10

Val Leu Val Thr Val Asn Tyr Pro Pro Thr Ile Thr Asp Val Thr Ser
1               5                   10                  15

Ala Arg

<210> SEQ ID NO 11
<211> LENGTH: 11
<212> TYPE: PRT
<213> ORGANISM: artificial
<220> FEATURE:
<223> OTHER INFORMATION: rodent IgLON5 fragment

<400> SEQUENCE: 11

Leu Leu Ser Ser Gly Ser Ala Glu Gly Leu Lys
1               5                   10

<210> SEQ ID NO 12
<211> LENGTH: 344
<212> TYPE: PRT
<213> ORGANISM: artificial
<220> FEATURE:
<223> OTHER INFORMATION: artificial IgLON5 construct

<400> SEQUENCE: 12

Met Asp Ala Tyr Phe Thr Glu Cys Ile Pro Ser Lys Thr Asn Lys Arg
1               5                   10                  15

Tyr Phe Tyr Asn Val Cys Val Thr Ala Leu Ala Gly Leu Ala Val Ile
                20                  25                  30

Ser Arg Gly Leu Leu Ser Gln Ser Leu Glu Phe Ser Ser Pro Ala Asp
            35                  40                  45

Asn Tyr Thr Val Cys Glu Gly Asp Asn Ala Thr Leu Ser Cys Phe Ile
        50                  55                  60

Asp Glu His Val Thr Arg Val Ala Trp Leu Asn Arg Ser Asn Ile Leu
65                  70                  75                  80

Tyr Ala Gly Asn Asp Arg Trp Ser Asp Pro Arg Val Arg Leu Leu
                85                  90                  95

Ile Asn Thr Pro Glu Glu Phe Ser Ile Leu Ile Thr Gln Val Gly Leu
                100                 105                 110

Gly Asp Glu Gly Leu Tyr Thr Cys Ser Phe Gln Thr Arg His Gln Pro
            115                 120                 125

Tyr Thr Thr Gln Val Tyr Leu Ile Val His Val Pro Ala Arg Ile Val
        130                 135                 140

Asn Ile Ser Ser Pro Val Ala Val Asn Glu Gly Gly Asn Val Asn Leu
145                 150                 155                 160

Leu Cys Leu Ala Val Gly Arg Pro Glu Pro Thr Val Thr Trp Arg Gln
                165                 170                 175

Leu Arg Asp Gly Phe Thr Ser Glu Gly Glu Ile Leu Glu Ile Ser Asp
            180                 185                 190

Ile Gln Arg Gly Gln Ala Gly Glu Tyr Glu Cys Val Thr His Asn Gly
        195                 200                 205

Val Asn Ser Ala Pro Asp Ser Arg Arg Val Leu Val Thr Val Asn Tyr
        210                 215                 220

-continued

```
Pro Pro Thr Ile Thr Asp Val Thr Ser Ala Arg Thr Ala Leu Gly Arg
225                 230                 235                 240

Ala Ala Leu Leu Arg Cys Glu Ala Met Ala Val Pro Pro Ala Asp Phe
                245                 250                 255

Gln Trp Tyr Lys Asp Asp Arg Leu Leu Ser Ser Gly Ser Ala Glu Gly
                260                 265                 270

Leu Lys Val Gln Thr Glu Arg Thr Arg Ser Met Leu Leu Phe Ala Asn
            275                 280                 285

Val Ser Ala Arg His Tyr Gly Asn Tyr Thr Cys Arg Ala Ala Asn Arg
            290                 295                 300

Leu Gly Ala Ser Ser Ala Ser Met Arg Leu Leu Arg Pro Gly Ser Leu
305                 310                 315                 320

Glu Asn Ser Ala Pro Arg Pro Pro Gly Pro Leu Thr Leu Leu Ser Ala
                325                 330                 335

Leu Ser Trp Leu Trp Trp Arg Met
                340
```

DIAGNOSIS OF A NEUROLOGICAL DISEASE

This application is a continuation of U.S. application Ser. No. 15/116,179, filed Aug. 2, 2016, which is a U.S. National Stage of International Application No. PCT/EP2015/052529, filed Feb. 6, 2015, which claims the benefit of and priority to European Patent Application No. 14154384.3, filed Feb. 7, 2014; the entire contents of each of the foregoing applications are hereby incorporated by reference herein.

The present invention concerns subject matter connected to or making use of IgLON5, IgLON5 fragments and variants of IgLON5 and IgLON5-fragments. In particular the present invention relates to a use of a polypeptide comprising one or more sequences of IgLON5, an IgLON5-fragment or a variant thereof for the diagnosis of a disease, a polypeptide comprising one or more sequences of IgLON5, an IgLON5-fragment or a variant thereof or a nucleic acid encoding said polypeptide for use in the treatment of a disease, an autoantibody binding to IgLON5, an IgLON5-fragment or a variant thereof, which is preferably for use in the diagnosis of a disease, a pharmaceutical composition comprising a polypeptide comprising one or more sequences of IgLON5, an IgLON5-fragment or a variant thereof, an in vitro method for diagnosing a disease, comprising the steps a1) contacting a liquid sample comprising an antibody from a subject with a polypeptide comprising one or more sequences of IgLON5, an IgLON5-fragment or a variant thereof, or a2) contacting a tissue sample comprising IgLON5, an IgLON5-fragment or a variant thereof from a subject with an antibody binding to IgLON5, the IgLON5-fragment or the variant thereof, and following steps a1) or a2), b) detecting formation of a complex comprising the antibody and IgLON5, the IgLON5-fragment or the variant thereof, an in vitro method for diagnosing a disease, preferably an autoimmune disease, comprising the step of detecting in a liquid sample comprising antibodies an autoantibody binding to IgLON5, a medical or diagnostic device comprising such autoantibody or such polypeptide, a test kit for the diagnosis of a disease, which test kit comprises the autoantibody and/or a polypeptide comprising one or more sequences of IgLON5, an IgLON5-fragment or a variant thereof, a method for isolating an autoantibody binding to IgLON5, an IgLON5-fragment or a variant thereof, comprising the steps a) contacting a sample comprising the autoantibody with a polypeptide comprising one or more sequences of IgLON5, the IgLON5-fragment or the variant thereof, which polypeptide is preferably immobilized, such that a complex is formed, b) isolating the complex formed in step a), c) dissociating the complex isolated in step b), and d) separating the autoantibody from the polypeptide comprising one or more sequences of IgLON5, the IgLON5-fragment or the variant thereof, and a method for treating a disease associated with one or more symptoms selected from the group comprising parasomnia, stridor, sleep apnea, gait instability, dysarthria, dysphagia, limb ataxia, vocal cord paralysis, choreic movements in the limbs and face, memory and attention deficits, apathy, depressed mood, akathisia and urinary disturbances in a subject, comprising the steps a) reducing the concentration of autoantibodies binding to IgLON5, an IgLON5-fragment or a variant thereof in the subject's blood and/or b) administering one or more immunosuppressive pharmaceutical substances.

Sleep disorders are among the most common complaints seen by general practitioners. It is estimated that, at any one time, approximately 30% of the general public are affected by a significant sleep problem. Persistent sleep loss or poor quality sleep affects emotional state and behaviour, cognitive function and performance at school or work, family cohesion and general quality of life, mental health and also physical wellbeing.

Sleep disorders are associated with a wide range of disorders, for example disabilities, psychiatric, neurological, endocrinological or other medical disorders. Therefore, patients who have one or more of such symptoms and seek medical attention are at risk of being misdiagnosed. This is all the more true if the sleeping disorder is likely to be linked to a neurodegenerative disease such as Alzheimer's disease or Parkinson's disease, since clinicians still have to rely, particularly at the early stages of the diseases, on examining the patient's cognitive abilities, which are hard to assess in an objective and conclusive manner. Final confirmation of the diagnosis is possible only through autopsy after death.

Whilst reliable biomarkers that may be used for diagnosis at an early stage or to corroborate differential diagnoses are available for other types of disorders such as autoimmune metabolic disorders, in particular autoimmunity in diabetes mellitus, they remain to be established as a widely accepted tool for the diagnosis of neurodegenerative diseases or related disorders.

The importance of an early diagnosis cannot be overemphasized. Many neurodegenerative disorders, most prominently Alzheimer's and Parkinson's diseases, cannot be cured, but drugs are available that may be used to slow down their progression. The earlier the diagnosis, the better the chances to exploit available drugs to the full benefit of the patient.

Notwithstanding the need for a diagnosis at an early stage of the disease, it is important to bear in mind that the result needs to be reliable which is not always the case. For example, a patient was diagnosed as having Alzheimers' disease in a case reported in the literature, although he actually suffered from the autoimmune disorder referred to as hashimoto encephalitis. Such patients may be denied adequate treatment and they continue to suffer, although administration of commercially available drugs, such as cortisone in the case of hashimoto encephalitis, would be likely to ameliorate their symptoms.

Therefore, a problem underlying the present invention is to provide an agent and a method for the diagnosis of a disorder associated with one or more symptoms from the group comprising parasomnia, stridor, sleep apnea, gait instability, dysarthria, dysphagia, limb ataxia, vocal cord paralysis, choreic movements in the limbs and face, memory and attention deficits, apathy, depressed mood, akathisia and urinary disturbances.

Another problem underlying the present invention is to provide a method for diagnosing a neurodegenerative disease associated with one or more of these symptoms, wherein the method does not require the clinician in charge to rely on the examination of the patient's cognitive abilities, preferably a method that involves a serological assay.

Another problem underlying the present invention is to provide a method for diagnosing a novel tauopathy identified by the inventors that remains to be designated and is associated with one or more symptoms from the group comprising associated with one or more symptoms selected from the group comprising parasomnia, stridor, sleep apnea, gait instability, dysarthria, dysphagia, limb ataxia, vocal cord paralysis, choreic movements in the limbs and face, memory and attention deficits, apathy, depressed mood, akathisia and urinary disturbances.

Another problem underlying the present invention is to provide an autoantibody that, when found in a liquid sample taken from a patient, indicates that said patient is suffering from a neurodegenerative disease, preferably a tauopathy, more preferably the novel tauopathy identified by the inventors.

The problem underlying the present invention is solved by the subject-matter of the attached independent and dependent claims.

In a first aspect the problem underlying the present invention is solved by a use of a polypeptide comprising one or more sequences of IgLON5, an IgLON5-fragment or a variant thereof for the diagnosis of a disease.

In a second aspect the problem underlying the present invention is solved by a polypeptide comprising one or more sequences of IgLON5, an IgLON5-fragment or a variant thereof or a nucleic acid encoding said polypeptide for use in the treatment of a disease.

In a third aspect the problem underlying the present invention is solved by an autoantibody binding to IgLON5, an IgLON5-fragment or a variant thereof, preferably for use in the diagnosis of a disease.

In a fourth aspect the problem underlying the present invention is solved by a pharmaceutical composition comprising a polypeptide comprising one or more sequences of IgLON5, an IgLON5-fragment or a variant thereof.

In a fifth aspect the problem underlying the present invention is solved by an in vitro method for diagnosing a disease, comprising the steps a1) contacting a liquid sample comprising an antibody from a subject with a polypeptide comprising one or more sequences of IgLON5, an IgLON5-fragment or a variant thereof, or a2) contacting a tissue sample comprising IgLON5, an IgLON5-fragment or a variant thereof from a subject with an antibody binding to IgLON5, the IgLON5-fragment or the variant thereof, preferably the autoantibody according the third aspect, and, following steps a1) or a2), b) detecting formation of a complex comprising the antibody and IgLON5, the IgLON5-fragment or the variant thereof, and/or in addition to steps a1)/a2) and b), c) examining the Human Leukocyte Antigen (HLA) type of the subject.

In a first embodiment of the fifth aspect, the complex is detected using immunofluorescence microscopy or spectroscopy, NMR spectroscopy, immunodiffusion, mass spectrometry, radioactivity, chemical crosslinking, surface plasmon resonance, native gel electrophoresis, chromatography and/or enzymatic activity.

In a sixth aspect, the problem underlying the present invention is solved by an in vitro method for diagnosing a disease, preferably an autoimmune disease, comprising the step of detecting in a liquid sample comprising antibodies an autoantibody binding to IgLON5.

In a seventh aspect the problem underlying the present invention is solved by a medical or diagnostic device comprising an autoantibody according to the third aspect of the invention or a polypeptide comprising one or more sequence of IgLON5, an IgLON5-fragment or a variant thereof.

In a eighth aspect the problem underlying the present invention is solved by a test kit for the diagnosis of a disease, which test kit comprises the autoantibody according to the third aspect of the present invention and/or a polypeptide comprising one or more sequences of IgLON5, an IgLON5-fragment or a variant thereof.

In a first embodiment of the both the seventh and the eighth aspect, the problem is solved by providing the polypeptide comprising one or more sequences of IgLON5, an IgLON5-fragment or a variant thereof in an immobilized form.

In a second embodiment of the eighth aspect, which is also an embodiment of the first embodiment of the eighth aspect, the test kit comprises a means for detecting a complex comprising an antibody and the polypeptide comprising one or more sequences of IgLON5, an IgLON5-fragment or a variant thereof, preferably, wherein the antibody is the autoantibody according to the third aspect of the present invention.

In a preferred embodiment of any aspect of the present invention, the disease is selected from the group comprising sleep disorders, neurodegenerative diseases and hypoventilation, preferably a neurodegenerative disease, more preferably a tauopathy.

In a preferred embodiment of any aspect of the present invention, the disease is associated with one or more symptoms, preferably two or more symptoms, more preferably three or more symptoms, still more preferably four or more symptoms selected from the group comprising parasomnia, stridor, sleep apnea, gait instability, dysarthria, dysphagia, limb ataxia, vocal cord paralysis, choreic movements in the limbs and face, memory and attention deficits, apathy, depressed mood, akathisia and urinary disturbances, which symptoms, most preferably, comprise one or more sleep problems, dysphagia and at least one of memory problems and depressed mood.

In a ninth aspect the problem underlying the present invention is solved by a method for isolating an autoantibody binding to IgLON5, an IgLON5-fragment or a variant thereof, comprising the steps a) contacting a sample comprising the autoantibody with a polypeptide comprising one or more sequences of IgLON5, the IgLON5-fragment or the variant thereof, which polypeptide is preferably immobilized, such that a complex is formed, b) isolating the complex formed in step a), c) dissociating the complex isolated in step b), and d) separating the autoantibody from the polypeptide comprising one or more sequences of IgLON5, the IgLON5-fragment or the variant thereof.

In a tenth aspect the problem underlying the present invention is solved by a method for treating a neurological disease associated with one or more symptoms selected from the group comprising parasomnia, stridor, sleep apnea, gait instability, dysarthria, dysphagia, limb ataxia, vocal cord paralysis, choreic movements in the limbs and face, memory and attention deficits, apathy, depressed mood, akathisia and urinary disturbancesin a subject, comprising the steps a) reducing the concentration of autoantibodies binding to IgLON5, an IgLON5-fragment or a variant thereof in the subject's blood and/or b) administering one or more immunosuppressive pharmaceutical substances, preferably selected from the group comprising rituximab, prednisone, methylprednisolone, cyclophosphamide, mycophenolate-mofetil, intravenous immunoglobulin, tacrolimus, cyclosporine, methotrexate, azathioprine and/or the pharmaceutical composition according to the fourth aspect of the present invention.

In a preferred embodiment of any aspect of the present invention, the sequence of IgLON5 is the sequence according to SEQ ID NO 1 and the sequence of the IgLON5-fragment is a sequence selected from the group comprising SEQ ID NO 2, SEQ ID NO 3, SEQ ID NO 4, SEQ ID NO 5, SEQ ID NO 6, SEQ ID NO 7, SEQ ID NO 8, SEQ ID NO 9 and SEQ ID NO 10 and, preferably, the polypeptide comprises all of the sequences SEQ ID NO 1 to SEQ ID NO 10.

In another preferred embodiment of any aspect of the present invention, the polypeptide comprising one or more sequences of IgLON5, an IgLON5-fragment or a variant thereof is provided in the form of a cell comprising a nucleic acid encoding said polypeptide or in the form of a tissue comprising said polypeptide or variant thereof.

The present invention is based on the inventors' surprising finding that neurodegenerative diseases, in particularly tauopathies exist that may be associated with the emergence of autoantibodies binding to IgLON5, an IgLON5-fragment or a variant thereof.

Furthermore, the present inventors have surprisingly found that a new type of tauopathy, exists that is associated with one or more of symptoms from the group comprising parasomnia, stridor, sleep apnea, gait instability, dysarthria, dysphagia, limb ataxia, vocal cord paralysis, choreic movements in the limbs and face, memory and attention deficits, apathy, depressed mood, akathisia and urinary disturbances. The inventors have surprisingly found that autoantibodies binding to IgLON5, an IgLON5-fragment or a variant thereof may be used to diagnose said disorder.

Furthermore, the present inventors have surprisingly found that autoantibodies binding to IgLON5, an IgLON5-fragment or a variant thereof may be used for the differential diagnosis of disorders characterised by one or more of symptoms from the group comprising parasomnia, stridor, sleep apnea, gait instability, dysarthria, dysphagia, limb ataxia, vocal cord paralysis, choreic movements in the limbs and face, memory and attention deficits, apathy, depressed mood, akathisia and urinary disturbances, in particular neurodegenerative diseases, preferably for distinguishing the novel tauopathy identified by the inventors from other types of neurodegenerative diseases, more preferably tauopathies associated with similar symptoms.

The present invention centers around a polypeptide comprising one or more sequences of IgLON5, an IgLON5-fragment or a variant thereof for use in diagnosis and treatment and antibodies, in particular autoantibodies binding to IgLON5, an IgLON5-fragment or a variant thereof. IgLON5 is a member of a family of cell adhesion molecules involved in the control of neuronal pathfinding and synaptogenesis (Hashimoto, T., Yamada, M., Maekawa, S., Nakashima, T., Miyata, S. (2008) IgLON cell adhesion molecule Kilon is a crucial modulator for synapse number in hippocampal neurons, Brain Res 2008; 1224: 1-11). It has been shown that the expression of IgLON family members affects the proliferation and cell size of type-1 astrocytes (Sugimoto, C., Morita, S., Miyata, S. (2012) Overexpression of IgLON cell adhesion molecules changes proliferation and cell size of cortical astrocytes, Cell Biochem Funct., 2012 July; 30(5):400-5), but their precise roles and the mechanisms underlying their actions remain to be elucidated.

Neither IgLON5 nor autoantibodies binding to IgLON 5 have been described in the prior art as linked, let alone causatively linked, to neurological diseases such as tauopathies, let alone useful for diagnosing them.

In a preferred embodiment, the polypeptide referred to as "IgLON5" has the sequence represented by NP_001094842.1, which, as all sequence accession numbers referred to throughout this application, refers to the sequence deposited in the NCBI data base, more specifically the version online on Dec. 4, 2013. However, the teachings of the present invention may not only be carried out using polypeptides, in particular a polypeptide comprising the full-length sequence of IgLON5, having the exact amino acid sequences referred to in this application explicitly, for example by name, sequence or accession number, or implicitly, but also using fragments or variants of such polypeptides.

The term "fragment", with regard to IgLON5, refers to a less than full length sequence of said protein, encompassing e.g. an amino acid sequence which is truncated at one or both termini by one or more amino acids. Alternatively or in addition, such peptide sequence may comprise internal deletions of one or more amino acids. Thereby the residual length of the fragment equals or exceeds the length of one or more continuous or conformational epitopes, e.g. 6, 7, 8, 9, 10, 11, 12, 20, 25, 30, 40, 50, 60, 70, 80, 90, 100 or more amino acids.

The term "variant" of IgLON5 or a fragment thereof relates to a polypeptide comprising amino acid sequences that are at least 70, 75, 80, 85, 90, 92, 94, 95, 96, 97, 98 or 99% identical to the reference amino acid, i.e. IgLON5 or a fragment thereof, wherein, more preferably, amino acids other than those essential for the biological activity, for example the ability of an antigen to bind specifically to an antibody, preferably autoantibody, more preferably an autoantibody binding to IgLON5, an IgLON5-fragment or a variant thereof from a patient suffering from the novel tauopathy identified by the inventors, or the fold or structure of the polypeptide are deleted or substituted, wherein one or more such essential amino acids may optionally be replaced in a conservative manner or additional amino acids may be inserted such that the biological activity of the polypeptide is preserved. The state of the art comprises various methods that may be used to align two given nucleic acid or amino acid sequences and to calculate the degree of identity, see for example Arthur Lesk (2008), Introduction to bioinformatics, Oxford University Press, 2008, 3rd edition. In a preferred embodiment, the ClustalW software (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007). Clustal W and Clustal X version 2.0. Bioinformatics, 23, 2947-2948) is used.

Such variants of IgLON5 and IgLON5-fragments may be prepared e.g. by introducing deletions, insertions or substitutions in nucleic acid sequences encoding them, or by chemical synthesis or modification. Moreover, variants of IgLON5 and IgLON5-fragments may also be generated by fusion with other known polypeptides or variants thereof and encompass active portions or domains, preferably having a sequence identity of at least 70, 75, 80, 85, 90, 92, 94, 95, 96, 97, 98 or 99% when aligned with the active portion of the reference sequence, wherein the term "active portion", as used herein, refers to an amino acid sequence, which is less than the full length amino acid sequence or, in the case of a nucleic acid sequence, codes for less than the full length amino acid sequence, respectively, but retains at least some of the biological activity. For example, an active portion of a protease is capable of hydrolysing peptide bonds in polypeptides, and an immunogenic polypeptide retains the ability to bind to an antibody or autoantibody and, preferably, when administered to mammals, causes an immune response to occur, more specifically the production of autoantibodies.

The term "variant" of a nucleic acid comprises nucleic acids the complementary strand of which hybridises, preferably under stringent conditions, to the reference or wild type nucleic acid. Stringency of hybridisation reactions is readily determinable by one of ordinary skilled in the art, and in generally is an empirical calculation dependent on probe length, washing temperature and salt concentration. In general longer probes require higher temperatures for proper annealing, while shorter probes less so. Hybridisation generally depends on the ability of denatured DNA to reanneal to complementary strands present in an environment below their melting temperature. The higher the degree of desired homology between the probe and hybridisable sequence, the higher the relative temperature which may be used. As a result it follows that higher relative temperatures would tend to make the reaction conditions more stringent, while lower temperature less so. For additional details and explanation of stringency of hybridisation reactions, see Ausubel, F. M. (1995), Current Protocols in Molecular Biology. John Wiley & Sons, Inc. Moreover, the person skilled take in the art may follow the instructions given in the manual Boehringer Mannheim GmbH (1993) The DIG System Users Guide for Filter Hybridization, Boehringer Mannheim GmbH, Mannheim, Germany and in Liebl, W., Ehrmann, M., Ludwig, W., and Schleifer, K. H. (1991) International Journal of Systematic Bacteriology 41: 255-260 on how to identify DNA sequences by means of hybridisation. In a preferred embodiment, stringent conditions are applied for any hybridisation, i.e. hybridisation occurs only if the probe is 70% or more identical to the target sequence. Probes having a lower degree of identity with respect to the target sequence may hybridise, but such hybrids are unstable and will be removed in a washing step under stringent conditions, for example lowering the concentration of salt to 2×SSC or, optionally and subsequently, to 0.5×SSC, while the temperature is, in order of increasing preference, approximately 50° C.-68° C., approximately 52° C.-68° C., approximately 54° C.-68° C., approximately 56° C.-68° C., approximately 58° C.-68° C., approximately 60° C.-68° C., approximately 62° C.-68° C., approximately 64° C.-68° C., approximately 66° C.-68° C. In a particularly preferred embodiment, the temperature is approximately 64° C.-68° C. or approximately 66° C.-68° C. It is possible to adjust the concentration of salt to 0.2×SSC or even 0.1×SSC. Nucleic acid sequences having a degree of identity with respect to the reference or wild type sequence of at least 70, 80, 90, 91, 92, 93, 94, 95, 96, 97, 98, 99% may be isolated. In a preferred embodiment, the term variant of a nucleic acid sequence, as used herein, refers to any nucleic acid sequence that encodes the same amino acid sequence and variants thereof as the reference nucleic acid sequence, in line with the degeneracy of the genetic code. A nucleic acid encoding IgLON5 has been deposited in the NCBI databases under accession number NM_001101372.

The polypeptide comprising one or more sequences of IgLON5, an IgLON5-fragment or a variant thereof, when used to carry out the teachings of the present invention, may be provided in any form and at any degree of purification, from tissues or cells comprising said polypeptide in an endogenous form, more preferably cells overexpressing the polypeptide, crude or enriched lysates of such cells, to purified and/or isolated polypeptide which is essentially pure. In a preferred embodiment, the polypeptide is a native polypeptide, wherein the term "native", as used herein, the term "native polypeptide", as used herein, refers to a folded polypeptide, more preferably to a folded polypeptide purified from tissues or cells, more preferably from mammalian cells or tissues, optionally from non-recombinant tissues or cells. In another preferred embodiment, the polypeptide is a recombinant protein, wherein the term "recombinant", as used herein, refers to a polypeptide produced using genetic engineering approaches at any stage of the production process, for example by fusing a nucleic acid encoding the polypeptide to a strong promoter for overexpression in cells or tissues or by engineering the sequence of the polypeptide itself. The person skilled in the art is familiar with methods for engineering nucleic acids and polypeptides encoded (for example, described in Sambrook, J., Fritsch, E. F. and Maniatis, T. (1989), Molecular Cloning, CSH or in Brown T. A. (1986), Gene Cloning an introduction, Chapman & Hall) and for producing and purifying native or recombinant polypeptides (for example Handbooks "Strategies for Protein Purification", "Antibody Purification", "Purifying Challenging Proteins", "Recombinant Protein Purification", "Affinity Chromatography", "Ion Exchange Chromatography", "Gel Filtration (Size Exclusion Chromatography)", "Hydrophobic Interaction Chromatography", "Multimodal Chromatography" (2009/2010), published by GE Healthcare Life Sciences, and in Burgess, R. R., Deutscher, M. P. (2009), Guide to Protein Purification). In a preferred embodiment, a polypeptide is pure if at least 60, 70, 80, 90, 95 or 99 percent of the polypeptide in the respective sample consists of said polypeptide as judged by SDS polyacrylamide gel electrophoresis followed by Coomassie blue staining and visual inspection.

If the polypeptide comprising one or more sequences of IgLON5, an IgLON5-fragment or a variant thereof is provided in the form of tissue, it is preferred that the tissue is from mammalian brain, for example human rat, primate, donkey, mouse, goat, horse, sheep or cow brain. If the polypeptide comprising one or more sequences of IgLON5, an IgLON5-fragment or a variant thereof is provided in the form of a non-recombinant cell, it is preferred that the cell is a neuron, preferably a hippocampal neuron or a cell from the neuropil of a mammal, for example rat, human, primate, donkey, mouse, goat, horse, sheep or cow. If a cell lysate is used, it is preferred that the cell lysate comprises the membranes associated with the surface of the cell. If the polypeptide comprising one or more sequences of IgLON5, an IgLON5-fragment or a variant thereof is provided in the form of a recombinant cell, it is preferred that the recombinant cell is a eukaryotic cell such as a yeast cell, more preferably a cell from a multicellular eukaryote such as a plant, mammal, frog or insect, most preferably from a mammal, for example rat, human, primate, donkey, mouse, goat, horse, sheep or cow. For example, a HEK293 cell transfected with a nucleic acid functionally encoding the polypeptide comprising one or more sequences of IgLON5, an IgLON5-fragment or a variant thereof may be used. The person skilled in the art is familiar with methods for preparing, transfecting and culturing such cells, for example those described in Phelan, M. C. (2001), Basic Techniques in Mammalian Cell Tissue Culture, John Wiley.

The polypeptide comprising one or more sequences of IgLON5, an IgLON5-fragment or a variant thereof used according to the present invention may be provided in any kind of conformation. For example, the polypeptide comprising one or more sequences of IgLON5, an IgLON5-fragment or a variant thereof may be an essentially unfolded, a partially or a fully folded polypeptide. In a preferred embodiment, the polypeptide comprising one or more sequences of IgLON5, an IgLON5-fragment or a variant thereof is folded in the sense that the IgLON5 epitopes comprised are part of folded domains and essentially adopt, in a more preferred embodiment, the fold adopted by the native protein in its natural environment. The person skilled in the art is familiar with methods suitable to determine whether or not a polypeptide is folded and if it is, which structure it has, for example limited proteolysis, NMR spectroscopy, CD spectroscopy or X-ray crystallography (see for example Banaszak L. J. (2008), Foundations of Structural Biology, Academics Press, or Teng Q. (2013), Structural Biology: Practical Applications, Springer), preferably multidimensional NMR spectroscopy is used. In a more preferred embodiment, the polypeptide comprising one or more sequences of IgLON5, an IgLON5-fragment or a variant thereof is folded such that it adopts the fold of the native protein in its natural environment and comprises one or more sequences selected from the group comprising SEQ ID NO 2, SEQ ID NO 3, SEQ ID NO 4, SEQ ID NO 5, SEQ ID NO 6, SEQ ID NO 7, SEQ ID NO 8, SEQ ID NO 9 and SEQ ID NO 10 or variants thereof, preferably all of them. The polypeptide comprising one or more sequences of IgLON5, an IgLON5-fragment or a variant thereof may be a fusion protein which comprises amino acid sequences other than IgLON5, an IgLON5-fragment or a variant thereof, in particular a C-terminal or N-terminal tag, preferably a C-terminal tag, which is, in a preferred embodiment, as used herein, an additional sequence motif or polypeptide having a function that has some biological or physical function and may, for example, be used to purify, immobilize, precipitate or identify the polypeptide comprising one or more sequences of IgLON5, an IgLON5-fragment or a variant thereof. In a more preferred embodiment, the tag is a sequence or domain capable of binding specifically to a ligand, for example a tag selected from the group comprising His tags, thioredoxin, maltose binding protein, glutathione-S-transferase, a fluorescence tag, for example from the group comprising green fluorescent protein (NCBI accession number: AAB51348.1), red fluorescent protein (AB038175.1), yellow fluorescent protein (AAA27544.1), orange fluorescent protein (AAP55761.1), blue fluorescent protein (YP_008577.1) or variants or known functional fluorescent homologues having other primary sequences thereof and their variants and/or an epitope tag, for example one selected from the group comprising myc, flag, HA and V5. In a preferred embodiment, the polypeptide carries a covalent modification such as a biotin tag.

According to the teachings of the present invention, an antibody, preferably an autoantibody binding to IgLON5, an IgLON5-fragment or a variant thereof may be used for the diagnosis of a disease. The person skilled in the art is familiar with methods for purifying antibodies, for example those described in Hermanson, G. T., Mallia, A. K., Smith, P. K. (1992), Immobilized Affinity Ligand Techniques, San Diego: Academic Press. Briefly, an antigen binding specifically to the antibody of interest, which antigen is IgLON5, an IgLON5-fragment or a variant thereof, is immobilized and used to purify, via affinity chromatography, the antibody of interest from an adequate source. A liquid sample comprising antibodies from a patient suffering from the novel tauopathy identified by the inventors may be used as the source.

The polypeptide comprising one or more sequences of IgLON5, an IgLON5-fragment or a variant thereof, when used within the present invention, may be an immobilized polypeptide. In a preferred embodiment, the term "immobilized", as used herein, refers to a molecule bound to a solid carrier insoluble in an aqueous solution, more preferably via a covalent bond, electrostatic interactions, encapsulation or entrapment, for example by denaturing a globular polypeptide in a gel, or via hydrophobic interactions, most preferably via one or more covalent bonds. Various suitable carriers, for example paper, metal, silicon or glass surfaces, microfluidic channels, membranes, beads such as magnetic beads, column chromatography media, biochips, polyacrylamide gels and the like have been described in the literature, for example in Kim, D., Herr, A. E. (2013), Protein immobilizsation techniques for microfluidic assays, Biomicrofluidics 7(4), 041501. This way, the immobilized molecule, together with the insoluble carrier, may be separated from an aqueous solution in a straightforward manner, for example by filtration, centrifugation or decanting. An immobilized molecule may be immobilized in a reversible or irreversible manner. For example, the immobilization is reversible if the molecule interacts with the carrier via ionic interactions that can be masked by addition of a high concentration of salt or if the molecule is bound via a cleavable covalent bond such as a disulphide bridge which may be cleaved by addition of thiol-containing reagents. By contrast, the immobilization is irreversible if the molecule is tethered to the carrier via a covalent bond that cannot be cleaved in aqueous solution, for example a bond formed by reaction of an epoxide group and an amine group as frequently used to couple lysine side chains to affinity columns. The protein may be indirectly immobilized, for example by immobilizing an antibody or other entity having affinity to the molecule, followed by formation of a complex to the effect that the molecule-antibody complex is immobilized. Various ways to immobilize molecules are described in the literature, for example in Kim, D., Herr, A. E. (2013), Protein immobilizsation techniques for microfluidic assays, Biomicrofluidics 7(4), 041501. In addition, various reagents and kits for immobilization reactions are commercially available, for example from Pierce Biotechnology.

The polypeptide used to carry out the inventive teachings is preferably designed such that it is immunogenic, more preferably such that it binds to autoantibodies binding to IgLON5, IgLON5-fragments or variants thereof from patients suffering from the novel tauopathy identified by the inventors. In one embodiment, such polypeptide comprises a stretch of 6, 7, 8, 9, 10, 11, 12, 20, 25, 30, 40, 50, 60, 70, 80, 90, 100 or more, preferably at least 9 but no more than 16, consecutive amino acids from NP_001094842.1 (IgLON5) or variants thereof. The person skilled in the art is familiar with guidelines used to design peptides having sufficient immunogenicity, for example those described in Jackson, D. C., Fitzmaurice, C. J., Brown, L. E., Zeng, W. (1999), Preparation and properties of totally synthetic immunogenes, Vaccine Volume 18, Issues 3-4, September 1999, Pages 355-361; and Black, M., Trent, A., Tirrell, M. and Olive, C. (2010), Advances in the design and delivery of peptide subunit vaccines with a focus on Toll-like receptor agonists, Expert Rev Vaccines, 2010 February; 9(2): 157-173. Briefly, it is desirable that the peptide meets as many as possible of the following requirements: (a) it has a high degree of hydrophilicity, (b) it comprises one or more residues selected from the group comprising aspartate, proline, tyrosine and phenylalanine, (c) is has, for higher specificity, no or little homology with other known peptides or polypeptides, (d) it needs to be sufficiently soluble and (e) it comprises no glycosylation or phosphorylation sites unless required for specific reasons. Alternatively, bioinformatics approaches may be followed, for example those described by Moreau, V., Fleury, C., Piquer, D., Nguyen, C., Novali, N., Villard, S., Laune, D., Granier, C. and Molina, F. (2008), PEPOP: Computational design of immunogenic peptides, BMC Bioinformatics 2008, 9:71.

In a preferred embodiment, the term "diagnosis", as used herein, refers to any kind of procedure aiming to find out whether a patient suffers or is likely or more likely than the average subject to suffer in the future from a disease or disorder in the past, at the time of the diagnosis or in the future, to find out how the disease is progressing or is likely to progress in the future or to evaluate the responsiveness of a patient with regard to a certain treatment, for example the administration of immunosuppressive drugs or drugs slowing down the progress of a neurodegenerative disease. In other words, the term diagnosis comprises not only diagnosing, but also prognosticating and/or monitoring the course of a disease or disorder. The person skilled in the art will appreciate that a clinician does usually not conclude whether or not the patient suffers or is likely to suffer from a disease, condition or disorders solely on the basis of a single diagnostic parameter, but needs to take into account other aspects, for example the presence of other autoantibodies, markers, blood parameters, clinical assessment of the patient's symptoms or the results of medical imaging or other non-invasive methods such as polysomnography, to arrive at a conclusive diagnosis. See Baenkler H. W. (2012), General aspects of autoimmune diagnostics, in Renz, H., Autoimmune diagnostics, 2012, de Gruyter, page 3. The value of a diagnostic agent or method may also reside the possibility to rule out one disease, thus allowing for the indirect diagnosis of another. Therefore, the terms "diagnosis" or does preferably not imply that the diagnostic methods or agents according to the present invention will be sufficient to finalize the diagnosis. In lieu or in addition to the inventive diagnostic method, one or more of the steps examination by way of polysomnography or Human Leukocyte Antigen Typing may be performed to diagnose the disease, preferably the novel tauopathy identified by the inventors. The person skilled in the art is familiar with these methods, which are also described in the state of the art, for example in Kryger, M. H, Roth T, Dement W C (2005), Principles and Practice of Sleep Medicine (4th ed.). Philadelphia: Elsevier Saunders, and in Zane, H. D. (2001) Immunology—Theoretical & Practical Concepts in Laboratory Medicine, W. B. Saunders Company, in particular in Chapter 14.

The inventive polypeptide comprising one or more sequences from IgLON5, an IgLON5-fragment or a variant thereof and/or a nucleic acid encoding said polypeptide may be used for the treatment of a disease, for the manufacture of a medicament for treating a disease and the like. The disease is preferably selected from the group comprising sleep disorders, neurodegenerative disease and hypoventilation and is preferably a neurodegenerative disease, more preferably a tauopathy, most preferably the novel tauopathy identified by the inventors.

The polypeptide comprising one or more sequences of IgLON5, an IgLON5-fragment or a variant thereof may be provided in the form of a cell comprising and/or expressing a nucleic acid encoding said polypeptide. If a nucleic acid comprising a sequence that encodes for the inventive polypeptide or variant thereof is used, such a nucleic acid may be an unmodified nucleic acid. In a preferred embodiment, the nucleic acid is a nucleic acid that, as such, does not occur in nature and comprises, compared to natural nucleic acid, at least one modification, for example an isotopic content or chemical modifications, for example a methylation, sequence modification, label or the like indicative of synthetic origin. In a preferred embodiment, the nucleic acid is a recombinant nucleic acid or part or a nucleic acid, and is, in a more preferred embodiment, part of a vector, in which it may be functionally linked with a promoter that allows for expression, preferably overexpression of the nucleic acid. In a preferred embodiment, said nucleic acid is inside a cell capable of expressing it to the effect that the inventive polypeptide or a variant thereof is made and, more preferably, routed to the surface of the cell. Said cell comprising the nucleic acid encoding the polypeptide comprising one or more sequences of IgLON5, an IgLON5-fragment or a variant thereof may be used according to the present invention. The person skilled in the art is familiar with methods used to synthesize, modify and amplify such a nucleic acid and to transfect cells using such a nucleic acid, preferably in a vector that allows for the transient or permanent maintenance or expression of the nucleic acid in the cell. The person skilled in the art is also familiar with suitable vectors, and many of them are commercially available, for example from Origene. For example, a vector encoding for fusion constructs with a C-terminal GFP may be used. The cell may be of eukaryotic or prokaryotic origin and is preferably a mammalian cell, for example a HEK293 cell. The cell comprising the nucleic acid encoding for the polypeptide comprising one or more sequences of IgLON5, an IgLON5-fragment or a variant thereof may be a recombinant cell or an isolated cell, wherein the term "isolated" means that the cell is enriched such that, compared to the environment of the wild type of said cell, fewer cells of other differentiation or species or in fact no such other cells are present.

According to the invention, an antibody, for example an autoantibody, is provided that is capable of binding specifically to IgLON5, an IgLON5-fragment or a variant thereof. In a preferred embodiment, the term "antibody", as used herein, refers to any immuglobulin-based binding moieties, more preferably one comprising at least one immunoglobulin heavy chain and one immunoglobulin light chain, including, but not limited to monoclonal and polyclonal antibodies as well as variants of an antibody, in particular fragments, which binding moieties are capable of forming a complex with an antigen. In a preferred embodiment, the term "binding specifically", as used herein, means that the binding is stronger than a binding reaction characterized by a dissociation constant of $1 \times 10^{-5}$ M, more preferably $1 \times 10^{-7}$ M, more preferably $1 \times 10^{-8}$ M, more preferably $1 \times 10^{-9}$ M, more preferably $1 \times 10^{-10}$ M, more preferably $1 \times 10^{-11}$ M, more preferably $1 \times 10^{-12}$ M, as determined by surface plasmon resonance using Biacore equipment. The antibody may be isolated or in a mixture comprising further antibodies, polypeptides, metabolites, cells and the like. In case the antibody is an autoantibody, it may be part of an autoantibody preparation which is heterogeneous or may be a homogenous autoantibody, wherein a heterogeneous preparation comprises a plurality of different autoantibody species as obtainable by preparation from the sera of human donors, for example by affinity chromatography using the immobilized antigen to purify any autoantibody capable of binding to said antigen. Preferably the antibody is an autoantibody, more preferably an autoantibody from the IgG class, most preferably from the group of subclasses comprising IgG1, IgG2 and IgG4, in particular IgG4. The antibody may be glycosylated or non-glycosylated. The person skilled in the art is familiar with methods that may be used for the identification, production and purification of antibodies and variants thereof, for examples those described in EP 2 423 226 A2 and references therein. The antibody may be used as a diagnostic agent, by itself, or in combination, for example as a complex, with the polypeptide comprising IgLON5, an IgLON5-fragment or a variant thereof.

The invention provides a pharmaceutical composition comprising a polypeptide comprising one or more sequences of IgLON5, an IgLON5-fragment or a variant thereof which is preferably suitable for administration to a subject, preferably a mammalian subject, more preferably to a human. Such a pharmaceutical composition may comprise a pharmaceutically acceptable carrier. The pharmaceutical composition may, for example, be administered orally, parenterally, by inhalation spray, topically, by eyedrops, rectally, nasally, buccally, vaginally or via an implanted reservoir, wherein the term "parentally", as used herein, comprises subcutaneous, intracutaneous, intravenous, intramuscular, intra-articular, intrasynovial, instrasternal, intrathecal, intralesional and intracranial injection or infusion techniques. The pharmaceutical composition may be provided in suitable dosage forms, for example capsules, tablets and aqueous suspensions and solutions, preferably in sterile form. It may be used in a method of treatment of a disease, which method comprises administering an effective amount of the polypeptide comprising IgLON5, an IgLON5-fragment or a variant thereof to a subject.

The present invention relates to a complex comprising an antibody binding to IgLON5, an IgLON5-fragment or a variant thereof. Such a complex may be used or detected as part of a method for diagnosing a disease. A liquid sample comprising antibodies from a subject may be used to practice the method. Such a liquid sample may be any bodily fluid comprising a representative set of antibodies from the subject, preferably a sample comprising antibodies of the IgG immunglobuline class from the subject, more preferably from the group comprising IgG1, IgG2 and IgG4 subclasses, most preferably from the IgG4 subclass. For example, a sample may be cerebrospinal fluid (CSF), blood or blood serum, lymph, insterstitial fluid and is preferably serum or CSF, more preferably serum.

In addition, the inventive method may comprise the step examining the Human Leukocyte Antigen (HLA) type of the subject, preferably by subjecting a blood sample taken from the patient to HLA typing. Detection of any allele from the group comprising HLA-DQB1*0501, HLA-DRB1*1001 and HLA-B27, preferably the combination of HLA-DQB1*0501 and HLA-DRB1*1001, indicates an increased risk that the patient suffers or will suffer from a disease, more preferably a neurological disease, more preferably a tauopathy, most preferably from the novel tauopathy identified by the inventors.

The step contacting a liquid sample comprising antibodies with a polypeptide comprising one or more sequences of IgLON5, an IgLON5-fragment or a variant thereof may be carried out by incubating an immobilized form of said polypeptide in the presence of the sample comprising antibodies under conditions that are compatible with the formation of the complex comprising said polypeptide and an antibody, preferably an autoantibody, binding to IgLON5, an IgLON5-fragment or a variant thereof. Optionally, the liquid sample, then depleted of antibodies binding to IgLON5, an IgLON5-fragment or a variant thereof, may subsequently be removed to facilitate detection of the complex. Optionally, one or more washing steps may be contemplated.

Alternatively, a sample comprising tissue comprising IgLON5, an IgLON5-fragment or a variant thereof rather than a liquid sample may be used. The tissue sample is preferably of neuronal origin and may be a sample of brain tissue, preferably taken from a brain section selected from the group comprising hypothalamus, prehypothalamic region and tegmentum of brainstem, more preferably cerebellum, for example rat cerebellum. Such a sample, which may be in the form of a tissue section fixed on a carrier, for example a glass slide for microscopic analysis, may then be contacted with the inventive antibody, preferably autoantibody, binding to IgLON5, the IgLON5-fragment or the variant thereof. The antibody is preferably labeled to allow for distinction from endogenous antibodies binding to IgLON5, the IgLON5-fragment or the variant thereof, so that newly formed complexes may be detected and, optionally, quantified. If the amount of complexes formed is lower than the amount found in a sample taken from a healthy subject, the subject from whom the sample examined has been taken is likely to suffer from a disease.

Any data demonstrating the presence or absence of the complex comprising the antibody and IgLON5, the IgLON5-fragment or the variant thereof may be correlated with reference data. For example, detection of said complex indicates that the patient who provided the sample analysed suffered, suffers or is likely to suffer in the future from the novel tauopathy identified by the inventors. If a patient has been previously diagnosed, the amount of complex detected in both runs may be correlated to find out about the progression of the disease and/or the success of a treatment. For example, if the amount of complex is found to increase, it may be concluded that the diseases is progressing and/or that any treatment attempted is unsuccessful.

The complex comprising the antibody and IgLON5, the IgLON5-fragment or the variant thereof may be detected using a variety of methods known to the person skilled in the art, for example immunofluorescence microscopy or spectroscopy, luminescence, NMR spectroscopy, immunodiffusion, radioactivity, chemical crosslinking, surface plasmon resonance, native gel electrophoresis or enzymatic activity. While some of these methods allow for the direct detection of the complex, it is preferred that one of the binding partners, preferably the antibody or, more preferably, a second antibody binding to the antibody, to IgLON5, the IgLON5-fragment or the variant thereof or to the polypeptide comprising one or more sequences of IgLON5, an IgLON5-fragment or a variant thereof, is labeled such that the complex may be detected specifically owing to intrinsic properties of the label, for example fluorescence, radioactivity, enzymatic activity, visibility in NMR or MRI spectra or the like. In a preferred embodiment the diagnosis or prognosis is carried out using a method selected from the group comprising western blot, dot blot, protein microarray, ELISA, line blot radioimmune assay and indirect immunofluorescence microscopy. Alternatively, more than one of these methods may be used in a complementary manner for more reliable results.

In a preferred embodiment, the prognosis, diagnosis, methods or test kit according to the present invention relates to a diagnostic method selected from the group comprising immunodiffusion techniques, immunoelectrophoretic techniques, light scattering immunoassays, light scattering immunoassays, agglutination techniques, labeled immunoassays such as those from the group comprising radiolabeled immunoassay, enzyme immunoassays, chemiluminscence immunoassays, and immunofluorescence techniques. The person skilled in the art is familiar with these methods, which are also described in the state of the art, for example in Zane, H. D. (2001), Immunology—Theoretical & Practical Concepts in Laboratory Medicine, W. B. Saunders Company, in particular in Chapter 14.

In a preferred embodiment, a line blot is used to carry out the diagnostic method according to the invention. The person skilled in the art is familiar with the experimental setup, which is described in the state of the art (Raoult, D., and Dasch, G. A. (1989), The line blot: an immunoassay for monoclonal and other antibodies. Its application to the serotyping of gram-negative bacteria. J. Immunol. Methods, 125 (1-2), 57-65; WO2013041540). Briefly, the one or more antigen of interest, in the case of the present invention the polypeptide comprising one or more sequences of IgLON5, an IgLON5-fragment or a variant thereof, may be attached to a carrier, for example nitrocellulose membrane, often in combination with additional antigens and controls. The nitrocellulose carrier is subsequently exposed to a sample comprising antibodies such as diluted serum. If the sample comprises an antibody binding to the antigen, a complex is formed which may be detected, preferably by incubation with a secondary antibody binding to the constant region of the first antibody, which secondary antibody comprises a detectable label, for example a radioactive isotope, a fluorescent dye or, in a preferred embodiment, an active enzyme fused or linked to the secondary antibody, such as alkaline phosphatase, which may be readily assayed using chromogenic substrates followed by simple visual examination. Suitable reagents, devices and software packages are commercially available, for example from EUROIMMUN, Lübeck, Germany.

In another preferred embodiment, the prognosis, diagnosis, methods or test kit in line with the inventive teachings contemplate the use of indirect immunofluorescence. The person skilled in the art is familiar with such techniques and the preparation of suitable samples, which are described in the state of the art (U.S. Pat. No. 4,647,543, Voigt, J., Krause, C., Rohwäder, E, Saschenbrecker, S., Hahn, M., Danckwardt, M., Feirer, C., Ens, K, Fechner, K, Barth, E, Martinetz, T., and Stöcker, W. (2012), Automated Indirect Immunofluorescence Evaluation of Antinuclear Autoantibodies on HEp-2 Cells," Clinical and Developmental Immunology, vol. 2012, doi:10.1155/2012/65105; Bonilla, E., Francis, L., Allam, F., et al., "Immunofluorescence microscopy is superior to fluorescent beads for detection of antinuclear antibody reactivity in systemic lupus erythematosus patients," Clinical Immunology, vol. 124, no. 1, pp. 18-21, 2007). Briefly, a carrier, such as a cover glass for use in microscopy, is coated with cells or tissue sections comprising the antigen, in the case of the present invention the polypeptide comprising one or more sequences of IgLON5, an IgLON5-fragment or a variant thereof. The carrier comprising the antigen is exposed to a patient sample comprising antibodies such as diluted serum. If the sample comprises an antibody binding to the antigen, the resulting complex may be detected, preferably by incubation with a secondary antibody comprising a fluorescent dye such as fluorescein, followed by visual examination using fluorescence microscopy. Suitable reagents, devices and software packages are commercially available, for example from EUROIMMUN, Lübeck, Germany.

Within the scope of the present invention, a medical or diagnostic device comprising an autoantibody or a polypeptide comprising one or more sequence of IgLON5, an IgLON5-fragment or a variant thereof according to the present invention is provided. Preferably such a medical or diagnostic device comprises the polypeptide comprising one or more sequences of IgLON5, an IgLON5-fragment or a variant thereof in a form that allows contacting it with an aqueous solution, more preferably the liquid human sample, in a straightforward manner. In particular, the polypeptide comprising one or more sequences of IgLON5, an IgLON5-fragment or a variant thereof may be immobilized on the surface of a carrier, which carrier comprises, but is not limited to glass plates or slides, biochips, microtiter plates, beads, for example magnetic beads, chromatography columns, membranes or the like. Exemplary medical devices include line blots, microtiter plates and biochips. In addition to the inventive polypeptide comprising one or more sequences of IgLON5, an IgLON5-fragment or a variant thereof, the medical or diagnostic device may comprise additional polypeptides, for example positive or negative controls or known other antigens binding to autoantibodies of diagnostic value, particularly those related other diseases associated with one or more symptoms selected from the group comprising parasomnia, stridor, sleep apnea, gait instability, dysarthria, dysphagia, limb ataxia, vocal cord paralysis, choreic movements in the limbs and face, memory and attention deficits, apathy, depressed mood, akathisia and urinary disturbances, which diseases are preferably selected from the group comprising sleep disorders, neurodegenerative disease and hypoventilation.

The inventive teachings provide a kit for diagnosing a disease associated with one or more symptoms selected from the group comprising stridor, sleep apnea, gait instability, dysarthria, dysphagia, limb ataxia, vocal cord paralysis, choreic movements in the limbs and face, memory and attention deficits, apathy, depressed mood, akathisia and urinary disturbances. Preferably the disease is selected from the group comprising sleep disorders, neurodegenerative diseases and hypoventilation. Such a kit may comprise instructions detailing how to use the kit and a means for contacting the polypeptide comprising one or more sequences of IgLON5, an IgLON5-fragment or a variant thereof with a bodily fluid sample from a subject, preferably a human subject, for example a line blot, wherein the polypeptide comprising one or more sequences of IgLON5, an IgLON5-fragment or a variant thereof is immobilized on the line blot. Furthermore, the kit may comprise a positive control, for example a batch of autoantibody or recombinant antibody known to bind to IgLON5, an IgLON5-fragment or a variant thereof and a negative control, for example a protein having no detectable affinity to IgLON5, an IgLON5-fragment or a variant thereof such as bovine serum albumin. Finally, such a kit may comprise a standard solution for preparing a calibration curve.

In a preferred embodiment the kit comprises a means for detecting a complex comprising the polypeptide comprising one or more sequences of IgLON5, an IgLON5-fragment or a variant thereof and an antibody binding to IgLON5, an IgLON5-fragment or a variant thereof. Such means is preferably an agent that binds to said complex and modifies the complex or carries a label such that makes the complex detectable. For example, said means may be a labeled secondary antibody binding to said polypeptide, at a binding site other than the binding site recognized by the primary antibody or to a constant region of the primary antibody. Alternatively, said means may be a crosslinking reagent chemically linking the antibody and the polypeptide comprising one or more sequences of IgLON5, an IgLON5-fragment or a variant thereof, so the complex may be identified on account of its increased molecular weight, for example by gel electrophoresis or size-exclusion chromatography The present invention provides a method for isolating an antibody, preferably an autoantibody, binding to a polypeptide comprising one or more sequences of IgLON5, an IgLON5-fragment or a variant thereof, comprising the steps a) contacting a sample comprising the antibody with a polypeptide comprising one or more sequences of IgLON5, an IgLON5-fragment or a variant thereof such that a complex is formed, b) isolating the complex formed in step a), c) dissociating the complex isolated in step b), and d) separating the antibody from the polypeptide comprising one or more sequences of IgLON5, an IgLON5-fragment or a variant thereof. A sample from a patient suffering from the novel tauopathy identified by the inventors may be used as the source of antibody. Alternatively the antibody may be a recombinant antibody. It is preferred that the polypeptide is immobilized, for example on the matrix of a column suitable for affinity chromatography or on a magnetic bead, since it is straightforward to separate the complex comprising the polypeptide and the antibody in step b) if such is the case. Subsequently, the antibody may be separated from the immobilized antigen in step c), for example by eluting the antibody by addition of an excess of non-immobilized antigen or by adding an agent interfering with intramolecular interactions, for example guanidinium chloride or sodium chloride at a high concentration, the latter if that electrostatic interactions are essential to maintain the complex. The person skilled in the art is familiar with methods to carry out each of these steps. Suitable methods are described in the state of the art, for example in the Handbooks "Affinity chromatography", "Strategies for Protein Purification" and "Antibody Purification" (2009/2010), published by GE Healthcare Life Sciences.

The inventions provides a method for treating the novel tauopathy identified by the inventors in a subject, comprising the steps a) reducing the concentration of autoantibodies binding to IgLON5, an IgLON5-fragment or a variant thereof in the subject's blood and/or b) administering one or more immunosuppressive pharmaceutical substances, preferably selected from the group comprising rituximab, prednisone, methylprednisolone, cyclophosphamide, mycophenolatemofetil, intravenous immunoglobulin, tacrolimus, cyclosporine, methotrexate, azathioprine and/or the pharmaceutical composition according to the present invention, wherein any other immunosuppressive pharmaceutical substances that may become available in the future may be used in lieu of or in addition to the substances specifically mentioned above. The concentration of autoantibodies binding to IgLON5, an IgLON5-fragment or a variant thereof may be reduced by obtaining from the patient blood, bringing it into contact with the polypeptide comprising one or more sequences of IgLON5, an IgLON5-fragment or a variant thereof, followed by separating and readministrating to the patient the blood depleted of autoantibodies binding to IgLON5, an IgLON5-fragment or a variant thereof. It is preferred that the polypeptide comprising one or more sequences of IgLON5, an IgLON5-fragment or a variant thereof is immobilized and the blood removed from the patient contacted with said immobilised polypeptide and readministered to the patient in a continuous manner. Alternatively the polypeptide comprising one or more sequences of IgLON5, an IgLON5-fragment or a variant thereof or the pharmaceutical composition according to the present invention may be administered to the patient to the effect that autoantibodies circulating in the patients' body form a complex with the administered complex rather than targeting endogenous IgLON5, IgLON5-fragments or variants thereof.

The person skilled in the art will appreciate that any of the preferred embodiments discussed throughout this application may be applied to any of the aspects of the inventions.

The present invention is further illustrated by the following figures and non-limiting sequences and examples from which further features, embodiments, aspects and advantages of the present invention may be taken.

BRIEF DESCRIPTION OF THE DRAWINGS

FIG. 2 shows polysomnograhic epochs illustrative of each sleep state, see also FIG. 1. A: Sleep onset characterized by undifferentiated NREM sleep with diffuse theta activity and rapid periodic leg movements that were particularly prominent at the left AT EMG channel; B: N2 sleep with K complexes in a chain of quadruplet (arrows), with frequent aperiodic muscular phasic activity in EMG surface of the limbs that correlate with gesticulations and vocalizations; C: REM sleep with typical rapid eye movements and EEG features with excessive phasic and tonic muscular activity and body jerks typical of REM sleep behaviors disorder; D: N3 with diffuse delta activity and well defined sleep spindles at 13 Hz (arrows) without body/limb movements. Abbreviations: EEG: electroencephalogram EMG; electromyogram; EOG: electrooculogram; Chin: Electromyography of mentalis muscle; EKG: Electrocardiogram; FDS: Flexor digitorum superficialis muscle left (L) and right (R); EDB: Extensor digitorum brevis muscle left (L) and right (R); AT: Anterior tibialis left (L) and right (R); NAS: Nasal air flow; THO: Thoracic respiratory movement; ABD; Abdominal respiratory movement; Note the calibration mark for time/EEG voltage.

FIG. 3 shows the reactivity of patient's antibodies with rat brain and cultures of hippocampal neurons. (A) Sagittal section of rat brain immunostained with a patient's CSF: there is a diffuse staining in the neuropil not seen when rat brain sections are incubated with a control CSF (B). The immunoreactivity was particularly robust in the cerebellum (C) where there was diffuse staining of the molecular layer and synaptic glomerula of the granular cell layer (D). (E) Culture of rat hippocampal neurons incubated (nonpermeabilized) with a patient's serum showing intense reactivity with a cell surface antigen. (D) Counterstained with hematoxylin. Scale bars in A and B=1000 μm, C=200 μm, D=50 μm and E=20 μm.

FIG. 7 shows Identification of IgLON5 protein by mass spectrometry. Proteomic results of two independent immunoprecipitation experiments with rat hippocampal neurons. Upper panels: Tables containing the sequences of the predicted peptides (three in A, experiment 1 and seven in B, experiment 2) matching the fragmentation spectra after mass spectrometry analysis. The probability of the peptide identification, XCorr score and DCn score calculated by Sequest program is also included. Lower panels: The identified peptides are shown in red within the complete rat IGLON5 protein (Swiss Prot accession number, IPI00367494) (14% of protein coverage in A and 29% in B).

Figure 1:
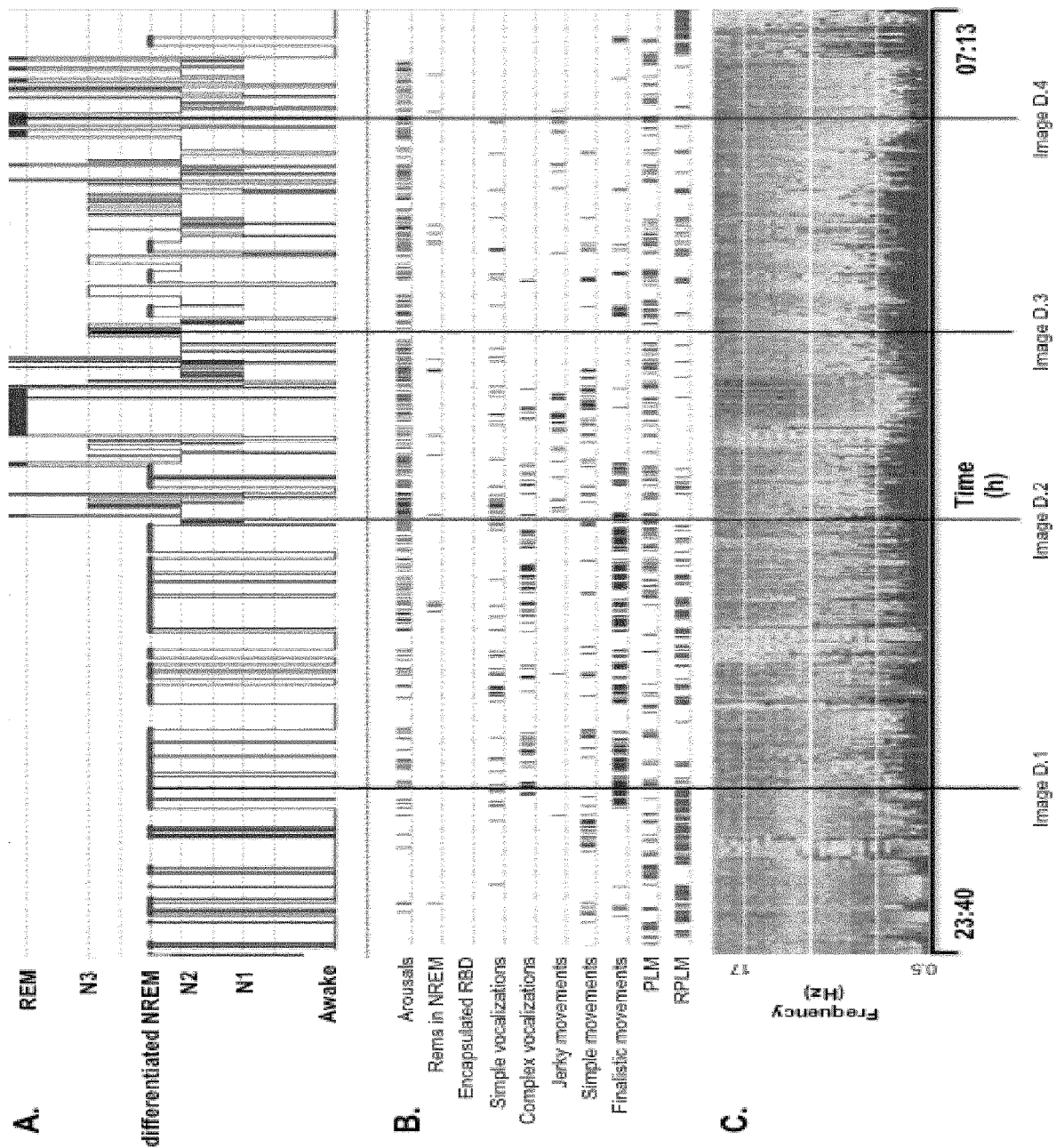
FIG. 1 shows a sleep recording in patient. A. Hypnogram; B. Arousals, dissociations and periodic movements; C. Density Spectral Array (DSA) showing the power spectrum of electroencephalographic frequencies (0-17 Hz) in electrode C3 referenced to electrode O2. Abbreviations: Rems Rapid eye movements; RBD: REM sleep behavior disorder; PLM: Periodic limb movements; RPLM: Rapid periodic leg movements.

Throughout this application, a number of sequences are disclosed which are referred to as:

SEQ ID NO 1: human IgLON5
SEQ ID NO 2: rodent/human IgLON5 fragment, see FIG. 7
SEQ ID NO 3: human IgLON5 fragment
SEQ ID NO 4: rodent/human IgLON5 fragment, see FIG. 7
SEQ ID NO 5: rodent/human IgLON5 fragment, see FIG. 7
SEQ ID NO 6: rodent/human IgLON5 fragment, see FIG. 7
SEQ ID NO 7: rodent/human IgLON5 fragment, see FIG. 7
SEQ ID NO 8: rodent/human IgLON5 fragment, see FIG. 7
SEQ ID NO 9: rodent/human IgLON5 fragment, see FIG. 7
SEQ ID NO 10: rodent/human IgLON5 fragment, see FIG. 7
SEQ ID NO 11: rodent IgLON5 fragment, see FIG. 7
SEQ ID NO 12: artificial IgLON5 construct, see FIG. 7

REFERENCES

Hashimoto, T., Yamada, M., Maekawa, S., Nakashima, T., Miyata, S. (2008) IgLON cell adhesion molecule Kilon is a crucial modulator for synapse number in hippocampal neurons, Brain Res 2008; 1224: 1-11

Sugimoto, C., Morita, S., Miyata, S. (2012) Overexpression of IgLON cell adhesion molecules changes proliferation and cell size of cortical astrocytes, Cell Biochem Funct., 2012 July; 30(5):400-5

Lesk, A. (2008), Introduction to bioinformatics, Oxford University Press, 2008, 3rd edition Thompson et al. (1994), Nucleic Acids Research 22, 4637-4680

Ausubel, F. M. (1995) Current Protocols in Molecular Biology, John Wiley & Sons Inc.

Boehringer Mannheim GmbH (1993) The DIG System Users Guide for Filter Hybridization, Boehringer Mannheim GmbH, Mannheim, Germany Liebl, W., Ehrmann, M., Ludwig, W., and Schleifer, K. H. (1991) International Journal of Systematic Bacteriology 41: 255-260

Hermanson, G. T., Mallia, A. K., Smith, P. K. (1992), Immobilized Affinity Ligand Techniques, San Diego: Academic Press Kim, D., Herr, A. E. (2013), Protein immobilization techniques for microfluidic assays, Biomicrofluidics 7(4), 041501.

Jackson, D. C., Fitzmaurice, C. J., Brown, L. E., Zeng, W. (1999), Preparation and properties of totally synthetic immunogens, Vaccine Volume 18, Issues 3-4, September 1999, Pages 355-361

Black, M., Trent, A., Tirrell, M. and Olive, C. (2010), Advances in the design and delivery of peptide subunit vaccines with a focus on Toll-like receptor agonists, Expert Rev Vaccines, 2010 February; 9(2): 157-173

Moreau, V., Fleury, C., Piquer, D., Nguyen, C., Novali, N., Villard, S., Laune, D., Granier, C. and Molina, F. (2008), PEPOP: Computational design of immunogenic peptides, BMC Bioinformatics 2008, 9:71

Robinson, M. K., Paszty, C. J., Lawson, A., Popplewell, A., and Henry, A. J. (2012) Antibody-based diagnostics and therapeutics, EP 2 423 226

Handbook "Affinity chromatography" (2009/2010), published by GE Healthcare Life Sciences Handbook "Strategies for Protein Purification" (2009/2010), published by GE Healthcare Life Sciences Handbook "Antibody Purification" (2009/2010), published by GE Healthcare Life Sciences Handbook "Purifying Challenging Proteins" (2009/2010), published by GE Healthcare Life Sciences Handbook "Recombinant Protein Purification" (2009/2010), published by GE Healthcare Life Sciences Handbook "Ion Exchange Chromatography" (2009/2010), published by GE Healthcare Life Sciences Handbook "Gel Filtration (Size Exclusion Chromatography)" (2009/2010), published by GE Healthcare Life Sciences Handbook "Hydrophobic Interaction Chromatography" (2009/2010), published by GE Healthcare Life Sciences Handbook "Multimodal Chromatography" (2009/2010), published by GE Healthcare Life Sciences Sambrook, J., Fritsch, E. F. and Maniatis, T. (1989), Molecular Cloning, CSH Brown, T. A. (1986), Gene Cloning—an introduction, Chapman & Hall Burgess, R. R., Deutsche, M. P. (2009), Guide to Protein Purification, Deutscher—2009

Phelan, M. C. (2001), Basic Techniques in Mammalian Cell Tissue Culture, John Wiley Banaszak, L. J. (2008), Foundations of Structural Biology, Academics Press Teng, Q., (2013), Structural Biology: Practical Applications, Springer Baenkler, H. W. (2012), General aspects of autoimmune diagnostics, in Renz H., Autoimmune diagnostics, 2012, de Gruyter, page 3

Kryger, M. H, Roth T, Dement W C (2005), Principles and Practice of Sleep Medicine, (4th ed.). Philadelphia: Elsevier Saunders.

Zane, H. D. (2001), Immunology—Theoretical & Practical Concepts in Laboratory Medicine, W. B. Saunders Company, in particular in Chapter 14

Iber, C., Ancoli-Israel, S., Chesson, A., and Quan, S. F. (2007), The AASM manual for the scoring of sleep and associated events: rules, terminology and technical specifications, 1st ed. Westchester, Ill.: American Academy of Sleep Medicine Santamaria, J., Högl, B., Trenkwalder, C., Bliwise, D. (2011), Scoring sleep in neurological patients: the need for specific considerations, Sleep 2011; 34:1283-4

Lancaster, E., Dalmau, J. (2012), Neuronal autoantigens-pathogenesis, associated disorders and antibody testing, Nat. Rev. Neurol. 2012; 8:380-90

Cornelius, J. R., Pittock, S. J., McKeon, A., et al. (2011), Sleep manifestations of voltage-gated potassium channel complex autoimmunity, Arch Neurol 2011; 68:733-8

Iranzo, A., Graus, F., Clover, L., et al. (2006), Rapid eye movement sleep behavior disorder and potassium channel antibody-associated limbic encephalitis, Ann Neurol 2006; 59:178-81

Montagna, P., Lugaresi, E. (2002), Agrypnia Excitata: a generalized overactivity syndrome and a useful concept in the neurophysiopathology of sleep, ClinNeurophysiol 2002; 113:552-60

Irani, S. R., Pettingill, P., Kleopa, K. A., et al. (2012), Morvan syndrome: clinical and serological observations in 29 cases, Ann Neurol 2012; 72:241-55

Dalmau, J., Gleichman, A. J., Hughes, E. G., et al. (2008), Anti-NMDA-receptor encephalitis: case series and analysis of the effects of antibodies, Lancet Neurol. 2008; 7:1091-8

Gelpi, E., Lladó, A., Clarimón, J., et al. (2012), Phenotypic variability within the inclusion body spectrum of basophilic inclusion body disease and neuronal intermediate filament inclusion disease in frontotemporal lobar degenerations with FUS-positive inclusions, J Neuropathol Exp Neurol 2012; 71:795-805

Raoult, D., and Dasch, G. A. (1989), The line blot: an immunoassay for monoclonal and other antibodies. Its application to the serotyping of gram-negative bacteria. J. Immunol. Methods, 125 (1-2), 57-65.

Meyer, W., and Scheper, T. (2013) Calibration strip for an immunoblot, WO2013041540

Stöcker, W. (1987) Process for analyses to be carried out on immobilized biological tissue, U.S. Pat. No. 4,647,543

Voigt, J., Krause, C., Rohwäder, E, Saschenbrecker, S., Hahn, M., Danckwardt, M., Feirer, C., Ens, K, Fechner, K, Barth, E, Martinetz, T., and Stöcker, W. (2012), Automated Indirect Immunofluorescence Evaluation of Antinuclear Autoantibodies on HEp-2 Cells," Clinical and Developmental Immunology, vol. 2012, doi:10.1155/2012/651058.

Bonilla, E., Francis, L., Allam, F., et al., "Immunofluorescence microscopy is superior to fluorescent beads for detection of antinuclear antibody reactivity in systemic lupus erythematosus patients," Clinical Immunology, vol. 124, no. 1, pp. 18-21, 2007.

EXAMPLES

Patients and Methods

Inclusion Criteria, Patients, and Controls

Three of the eight patients (patients 1-3, Table 1) of this study were from the cohort of patients studied in the multidisciplinary sleep disorders unit of Hospital Clinic, Barcelona, Spain. The remaining five patients were identified among samples sent to our laboratory with similar immunohistochemical reactivity. Serum or CSF of 251 patients were used as controls including 45 with pathologically confirmed Alzheimer disease, 28 with clinical diagnosis of progressive supranuclear palsy, 21 with DNA-binding protein 43 (TDP-43) frontotemporal dementia, 18 with multiple system atrophy, 25 with idiopathic RBD, 28 with hypocretin deficient narcolepsy, 54 with multiple sclerosis, and 32 with anti-Lgi1 encephalitis. Brain tissue, serum and CSF samples used in the study are deposited in the Neurological Tissue Bank and the Biobank of the Institut d'Investigacions Biomèdiques August Pi i Sunyer, Barcelona, Spain.

Polysomnographic (PSG) Studies

Nocturnal video-polysomnography included electrooculography, electroencephalography (F3, F4, C3, C4, O1 and O2, referred to combined ears), submental EMG, surface EMG of the right and left anterior tibialis, flexor digitorum superficialis in the upper limbs, and the extensor digitorum brevis in the lower limbs. Electrocardiography, nasal and oral airflow, thoracic and abdominal movements, and oxyhemoglobin saturation were also recorded.

We scored "undifferentiated NREM sleep" epochs of irregular theta EEG slowing, clearly different from the awake alpha rhythm, and lacking vertex sharp waves, K complexes, sleep spindles or delta slowing, and without definite and recurrent rapid eye movements, such as those typically seen in later periods of REM sleep. We scored "stage N2" epochs with definite K complexes or spindles at 12-14 Hz, even if associated with excessive EMG activation and movements or occasional rapid eye movements of low amplitude than those typical of the REM sleep in the same patient. "Encapsulated rapid eye movement sleep behavior disorder (RBD) during NREM sleep" occurred when an episode lasting few seconds contained rapid eye movements, excessive EMG twitching and typical RBD jerks together with EEG features of REM sleep within an epoch of NREM sleep. Vocalizations were scored as simple and complex in each epoch, and body/limb movements as jerks, simple or finalistic depending upon their video characteristics (jerks were sudden contractions of a single or several muscle groups; finalistic were movements following a pattern that clearly reminded an identifiable daytime activity—e.g. eating, drinking, manipulating objects, etc.; and simple were the movements that were more complex than jerks but no so elaborated as the finalistic ones). We defined rapid periodic leg movements as those periodic leg movements that occurred with an interval between movements shorter than 5 seconds.

Four patients were recorded with video-PSG several nights throughout their clinical course at the sleep laboratory of the Hospital Clinic of Barcelona (Patients 1-3 and 5), and one patient at the sleep laboratory in Ulm, Germany (Patient 7). In total nineteen video-PSG were recorded. EMG was recorded in the submentalis muscle and both upper and lower limbs. Sleep stages and associated events were scored according to the 2007 American Academy of Sleep Medicine criteria (Iber C., Ancoli-Israel S., Chesson A., and Quan S. F. (2007), The AASM manual for the scoring of sleep and associated events: rules, terminology and technical specifications, 1st ed. Westchester, Ill.: American Academy of Sleep Medicine) or with the modifications previously proposed when the standard criteria could not be followed (Santamaria J., Högl B., Trenkwalder C., Bliwise D. (2011), Scoring sleep in neurological patients: the need for specific considerations, Sleep 2011; 34:1283-4).

Procedures for Detection of IgLON5 Antibodies and Characterization of the Antigen Female Wistar rats were euthanized and the brain was removed, sagittally sectioned, immersed in 4% paraformaldehyde at 4° C. for 1 hour, cryoprotected with 40% sucrose for 24 hours, and snap frozen in chilled isopentane. Immunohistochemistry using a standard avidin-biotin peroxidase method was applied using patients' serum (diluted 1:200) or CSF (1:5), followed by the appropriate secondary antibody, as reported (Lancaster E., Dalmau J. (2012), Neuronal autoantigens—pathogenesis, associated disorders and antibody testing, Nat. Rev. Neurol. 2012; 8:380-90). To study the distribution of IgG subclasses of the antibody, the same immunohistochemistry technique was used changing the secondary antibody by biotinylated mouse monoclonal antibodies to human IgG 1-4 subclasses (Sigma, St. Louis, Mo.) (dilutions: anti-IgG1 1:100, anti IgG2 1:200, anti-IgG3 1:200, and anti-IgG4 1:200) or to human IgM (Southern Biotechnology Associates, Inc., Birmingham, Ala., USA) as described (Cornelius J. R., Pittock S. J., McKeon A., et al. (2011), Sleep manifestations of voltage-gated potassium channel complex autoimmunity, Arch. Neurol. 2011; 68:733-8).

To show if anti-IgLON5 antibodies of different patients recognized similar epitopes, rat brain sections were pre-incubated with undiluted anti-IgLON5-positive serum for three hours followed by a biotinylated IgG obtained from another positive anti-IgLON5 serum, in 10% normal human serum, overnight at 4° C., and the Vectastain Elite ABC complex (Vector Labs, USA) for 40 min. The reaction was developed with 0.05% diaminobenzidine with 0.01% hydrogen peroxide in phosphate-buffered saline (PBS) with 0.5% Triton X-100. As controls, sections were incubated with biotinylated IgG from a normal human serum.

Rat hippocampal neuronal cultures were prepared as reported (Iranzo A., Graus F., Clover L., et al. (2006), Rapid eye movement sleep behavior disorder and potassium channel antibody-associated limbic encephalitis, Ann Neurol 2006; 59:178-81). Fourteen days live neurons grown on coverslips were treated for 1 hour at 37° C. with patients' or control serum (final dilution 1:750) or CSF (1:30). After removing the media and extensive washing with PBS, neurons were fixed with 4% PFA, and incubated with anti-human IgG Alexa Fluor secondary antibody diluted 1:1000 (Molecular Probes, OR). Results were photographed under a fluorescence microscope using Zeiss Axiovision software (Zeiss, Thornwood, N.Y.) (Montagna P., Lugaresi E. (2002), Agrypnia Excitata: a generalized overactivity syndrome and a useful concept in the neurophysiopathology of sleep, ClinNeurophysiol 2002; 113:552-60).

Immunoprecipitation experiments were done with cultures of rat hippocampal neurons grown in 100 mm wells, and incubated at 37° C. with patients' or control serum (diluted 1:100) for 1 hour. Neurons were then washed with PBS, lysed with buffer containing protease inhibitors (P8340; Sigma Labs, St. Louis, Mo., USA), and centrifuged for 20 minutes at 4° C. The supernatant was retained, incubated with protein A/G agarose beads (20423; Pierce, Rockford, Ill.) overnight at 4° C., and centrifuged. The pellet was resuspended in Laemmli buffer, boiled for 10 minutes, separated in a 10% sodium dodecyl sulphate polyacrylamide gel electrophoresis, and the proteins visualized with EZBlue gel staining (G1041; Sigma Labs). Because the EZBlue gel staining did not identify specific protein bands, gels were cut into ten slices and sent for mass spectrometry to the Proteomics Core Facility at the University of Pennsylvania. Protein bands were trypsin digested and analyzed with a nano liquid chromatography (nano LC)/nanospray/linear ion trap (LTQ) mass spectrometer (Thermo Electron Corporation, San Jose, Calif.) as reported (Irani S. R., Pettingill P., Kleopa K. A., et al. (2012), Morvan syndrome: clinical and serological observations in 29 cases, Ann Neurol 2012; 72:241-55). The Xcalibur software (Thermo Scientific, Waltham, Mass.) was utilized to acquire the raw data and Sequest program (ThermoFinnigan, San Jose, Calif.; version SRF v. 5) to match the results with the UniProtKB/Swiss-Prot protein sequence database. The Scaffold 3.3 program was used to analyse the files generated. Protein identifications were accepted if they could be established at greater than 95.0% probability and contained at least three identified peptides.

To further confirm the specificity of the antigen, HEK293 cells were transfected with plasmids containing IgLON1, 2, 3, 4, and 5 (GFP-tagged clones from Origene: RG213594, RG226879, RG207618, RG216034, RG225495) as described (Dalmau J., Gleichman A. J., Hughes E. G., et al. (2008), Anti-NMDA-receptor encephalitis: case series and analysis of the effects of antibodies, Lancet Neurol. 2008; 7:1091-8). Cells were grown for 24 hours after transfection, incubated for 1 hour at 37° C. with patients' or control serum (final dilution 1:40) or CSF (1:2), and fixed with 4% paraformaldehyde, and permeabilized with 0.2% Triton X-100 (Sigma, Saint Louis, Mo.). Immunolabeling was performed using the appropriate Alexa-Fluor secondary antibodies diluted 1:1000 (Molecular Probes, OR) (Dalmau J., Gleichman A. J., Hughes E. G., et al. (2008), Anti-NMDA-receptor encephalitis: case series and analysis of the effects of antibodies, Lancet Neurol. 2008; 7:1091-8).

To rule out the possibility of additional neuronal antibodies, serum diluted 1:200 was serially incubated with six wells containing live HEK293 cells expressing IgLON5 or cells transfected with plasmids without insert. After sequential passes of one hour each, the serum was applied to sections of rat brain and live hippocampal neurons and the reactivity developed using the methods described above.

Neuropathological Studies

Neuropathologic examination was performed according to standardized protocols at the Neurological Tissue Bank of the IDIBAPS Biobank in two patients (patients 2 and 5 Table 1) (Gelpi E., Lladó A., Clarimón J., et al. (2012), Phenotypic variability within the inclusion body spectrum of basophilic inclusion body disease and neuronal intermediate filament inclusion disease in frontotemporal lobar degenerations with FUS-positive inclusions, J Neuropathol Exp Neurol 2012; 71:795-805). Immunohistochemistry was performed applying a panel of primary antibodies (Table 1S) as described (Gelpi E., Lladó A., Clarimón J., et al. (2012), Phenotypic variability within the inclusion body spectrum of basophilic inclusion body disease and neuronal intermediate filament inclusion disease in frontotemporal lobar degenerations with FUS-positive inclusions, J Neuropathol Exp Neurol 2012; 71:795-805). To evaluate the expression of IgLON5 in the areas more affected by tau pathology, sections from one of the autopsy cases and similar areas from a patient with Alzheimer disease were incubated, with a commercial antibody against IgLON5 (Abcam, Cambridge, UK) and the immunoreactivity visualized with the avidin-biotin immunoperoxidase method.

Results

Clinical Findings

The eight patients (5 women; age range: 52 to 76 years) had a prominent sleep disorder characterized by abnormal sleep movements and behaviors and obstructive sleep apneas with stridor. Five patients (patients 1-4 and 8, Table 1) were initially diagnosed of isolated obstructive sleep apnea syndrome. However, continuous positive airway pressure (CPAP) therapy improved the stridor and obstructive sleep apnea but not the other sleep symptoms. In four patients (Patients 1 to 4, Table 1), the sleep disorder was the presenting and most prominent complaint during the entire course of the disease. In addition to the sleep disorder, two patients (Patients 5 and 6) developed severe gait difficulties with loss of balance and gait failure, dysarthria, dysphagia, vocal cord paralysis, and central hypoventilation that was the cause of death in less than 6 months. The last two patients (Patients 7 and 8) had a chronic progressive evolution that started with frequent falls and gait instability followed by dysarthria, dysphagia, limb ataxia, and choreic movements in the limbs and face. In addition most patients developed mild memory and attention deficits with apathy, depressed mood, akathisia, or urinary disturbances. None of the patients developed parkinsonism or oculomotor signs compatible with the diagnosis of progressive supranuclear palsy. The clinical features and outcome are described in detail in Table 1.

Brain MRI, routine electroencephalogram, and CSF analysis were unremarkable. Nerve conduction studies and EMG done in seven patients ruled out neuromyotonia. CSF hypocretin levels obtained in three patients were normal. Human leukocyte antigen (HLA) typing was performed in four patients and all showed the HLA-DQB1*0501 and HLA-DRB1*1001 alleles. Three of them (patients 1-3) were also HLA-B27 positive. All patients received some type of immunotherapy without substantial improvement. Six patients are dead and all had sudden death or presented severe central hypoventilation (Table 1).

Polysomnographic Studies

The most prominent features of PSG studies are summarized in FIG. 1 and Table 2. Total sleep time was slightly reduced (sleep efficiency 68-88%; normal >85%). In four patients, sleep onset was accompanied by rapid periodic leg movements (FIG. 2A, video segment 1). Initiation of sleep, as well as reentering sleep after midnight awakenings, was abnormal in all five patients, either as an undifferentiated NREM sleep, in four patients, or poorly structured N2 sleep in one. There were frequent vocalizations, simple non-purposeful or finalistic movements with a pattern resembling daytime activities such as eating, drinking or manipulating objects (FIG. 2B, video segments 2-5). Normal N1 sleep was absent and well-structured N2 sleep with K complexes and spindles was rare. REM sleep was recorded in 16 out of the 19 PSG recordings and always in the form of RBD of mild to moderate severity (FIG. 2C). In all patients, clear periods of delta slowing typical of N3 sleep with frequent spindles and without vocalizations or movements, were recorded. Finally, all patients presented a sleep breathing disorder with stridor and moderate-severe obstructive sleep apneas (apnea-hypoapnea index without CPAP ranging from 20 to 84 apneas-hypoapneas per hour; normal 5) that were worse during quiet N3 sleep.

There was a characteristic distribution throughout the night of these sleep abnormalities (present in 14 out of the 19 PSG recordings). Periods of undifferentiated NREM and poorly structured N2 with finalistic movements predominated and were of longer duration after onset of nocturnal sleep or following awakenings in the first half of the night. Normal N3 sleep and RBD were more frequent and lasted longer in the second half of the night (FIG. 2D).

Antibody Characterization

The serum of the eight patients, and the five CSF available, showed an identical pattern of reactivity with the neuropil of rat brain. The immunoreactivity was more intense in the molecular layer and synaptic buttons of the granular layer of the cerebellum (FIG. 3). All sera and CSF labeled the membrane of live neurons in culture indicating the antigen was exposed on the cell surface (FIG. 3). Immunocompetition assays showed that all samples blocked the reactivity of the biotinylated IgG obtained from the serum of Patient 1 strongly suggesting that the antibodies of the eight patients reacted with the same epitopes.

Figure 4:
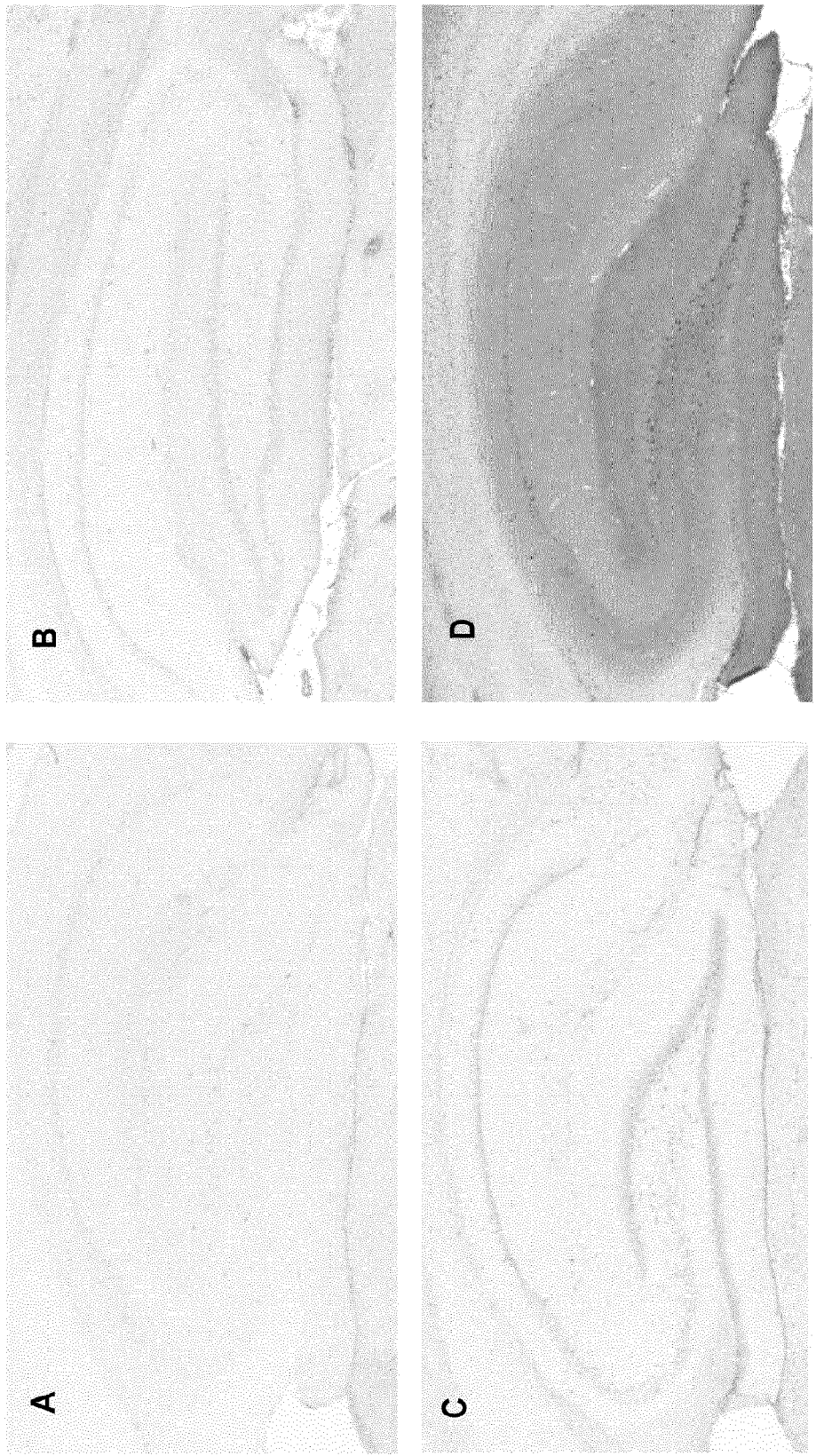
FIG. 4 shows the IgG isotype analysis of antibodies against IgLON5. Reactivity of a patient's serum with rat hippocampus after incubation with antibodies specific for human IgGI (A), IgG2 (B), IgG3 (C), and IgG4 (D). Robust neuropil immunostaining is only observed with IgG4. Scale bar=200 μm.

Initial serum antibody titers ranged from 1/5000 to 1/40000. In four patients, the titers decreased more than two-fold in the follow-up samples obtained after immunotherapy (Table 1). By contrast, no change in antibody titers was observed in the follow-up of another patient during the year that he was not treated. Analysis of IgG subclasses showed that in all patients the novel neuropil-reacting antibody was IgG4 (FIG. 4); one patient had additional IgG2, and four had very mild IgG1 reactivity. None of the patients had IgM antibody reactivity.

Identification of IgLON Family Member 5 as the Targeted Antigen

Figure 5:
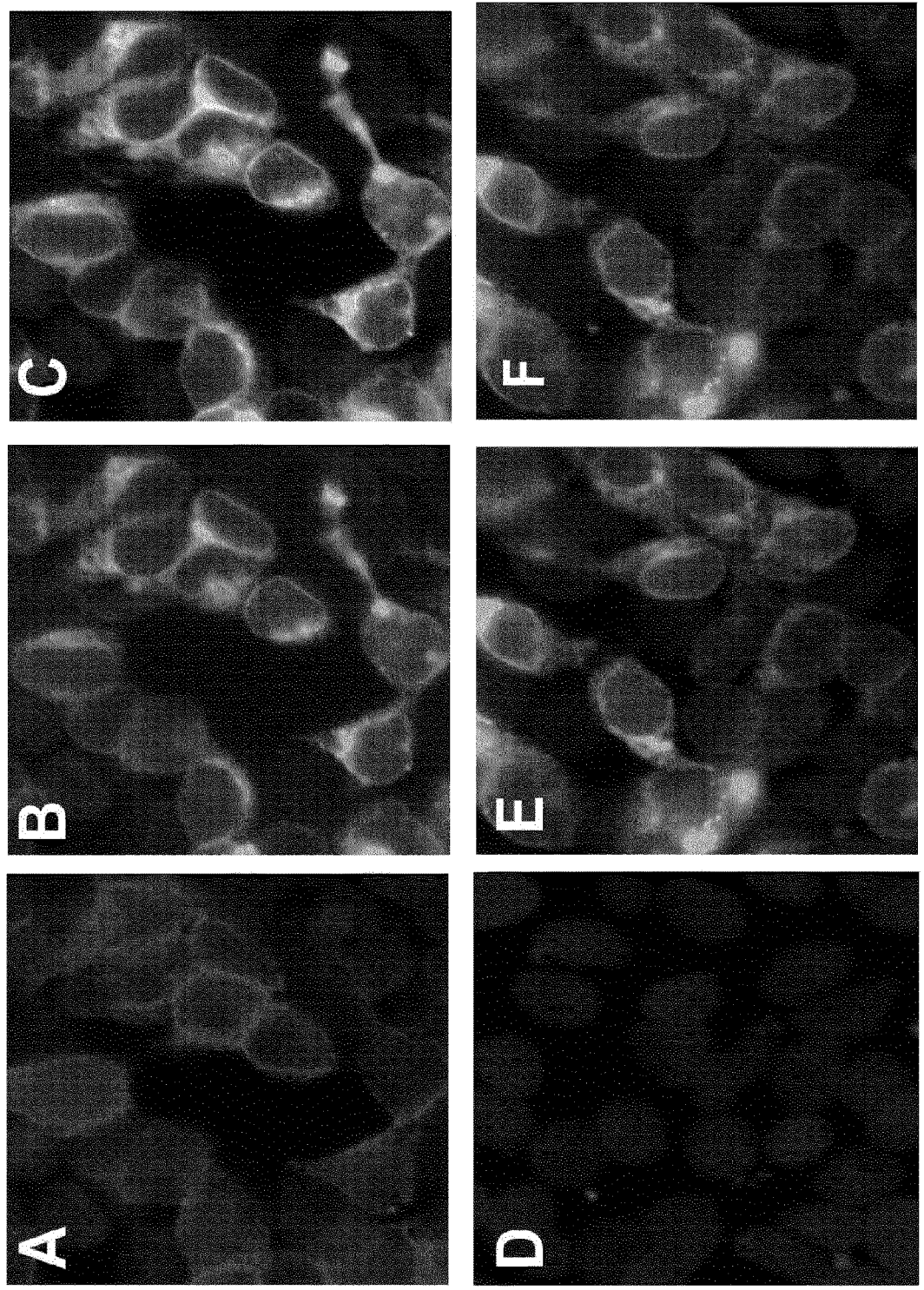
FIG. 5 shows the detection of IgLON5 antibodies using a HEK293 cell based assay. HEK293 cells were transfected to express EGFP-tagged IgLON5 and incubated live, not permeabilized, with a patient's (A-C) or control (D-F) serum. Patient's serum, but not control serum, stained the cell surface of cells (lighter grey) that specifically express IgLON5, as demonstrated by the EGFP fluorescence (lighter grey). Both reactivities are shown merged in C. Nuclei counterstained with DAPI. Scale bar=20 μm.

Mass spectrometry analysis revealed IgLON5 in two independent immunoprecipitation experiments using the serum of two patients. In every experiment we included as negative control a normal human serum. Seven peptides containing 29% of the protein sequence, and 3 peptides containing 14% of the protein sequence of IGLON5 were isolated using the antibodies of the two patients (FIG. 7). To further confirm the specificity of patients' antibodies for IgLON5, HEK293 cells transfected with plasmids coding each of the five members of the IgLON family were used in a cell-based assay (CBA). The serum and CSF of the eight patients only reacted with cells transfected with the GFP-tagged IgLON5 (FIG. 5). Sera did not react with HEK cells transfected with GFP-tagged IgLON1, 2, 3 or 4, thus confirming the antibody reactivity was specific for IgLON5 and not directed to the GFP tag (not shown). Analysis of serum or CSF of the 251 controls using the IgLON5 CBA identified a patient with antibodies in serum, but not CSF, who had been clinically diagnosed with progressive supranuclear palsy. The rest of the controls were negative.

Figure 8:
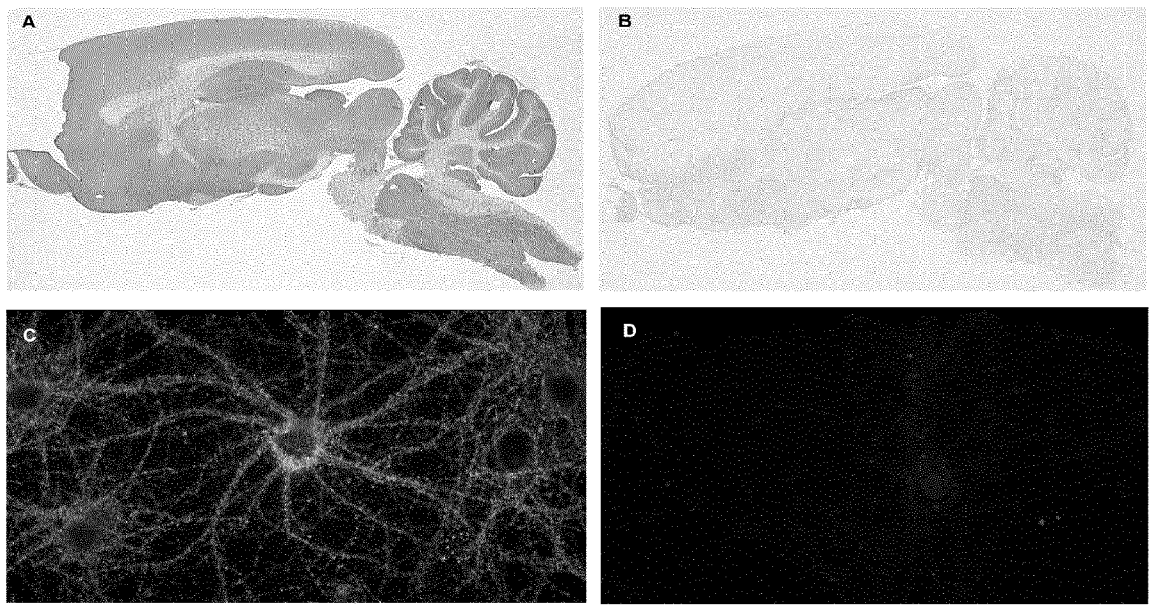
FIG. 8 shows Immunoabsorption with IgLON5. IgLON5 antibody-positive serum absorbed with HEK cells transfected with or without IgLON5. Only serum absorbed with HEK cells transfected with IgLON5 did not react with the neuropil of rat brain (B) and cultures of rat hippocampal neurons (D). IgLON5 reactivity was preserved when the serum was absorbed with non-transfected HEK cells (A, C). Scale bar A and B=1000 µm, C and D=20 µm.

To determine if patients' serum contained additional antibodies that could explain the additional symptoms of some cases (e.g., ataxia, hypoventilation), we immunoabsorbed the serum of three patients with different clinical course (Patients 1, 5, 7) with HEK293 cells expressing IgLON5 or cells transfected with plasmids without insert. The absorption with IgLON5 completely abrogated the reactivity of the three sera with rat brain and hippocampal neurons indicating that patients' antibodies were directed only against IgLON5 (FIG. 8).

Neuropathological Examination

Figure 6:
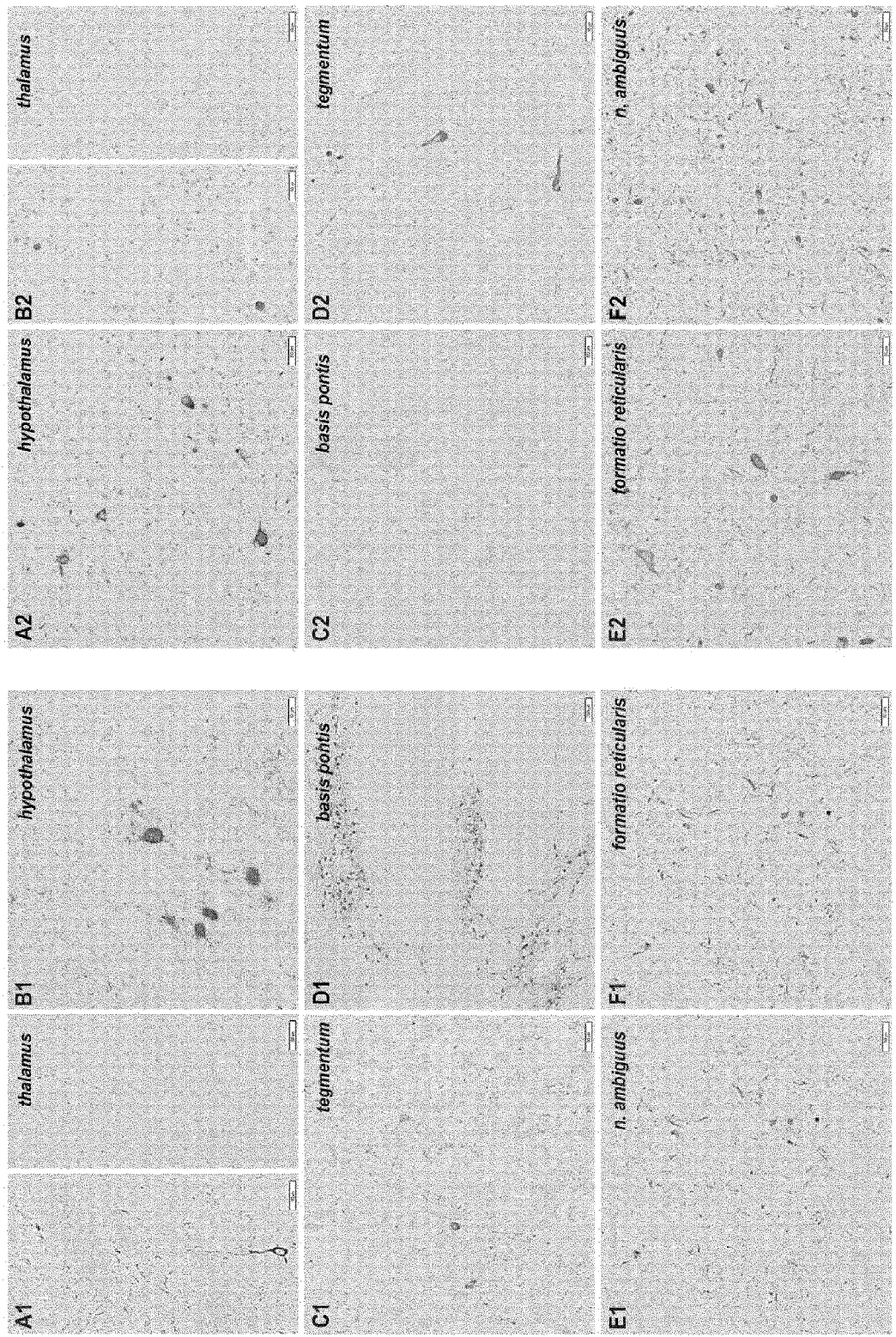
FIG. 6 shows the distribution of tau pathology. Panels A1-F1 correspond to patient 2, and panels A2-F2 correspond to patient 5. Moderate amounts of AT8 immunoreactive neuropil threads and neurofibrillary tangles are detected in hypothalamic nuclei (B1, A2. posterior hypothalamic nucleus; example of score ++) and anterior thalamus (A1, B2: left figure), but are completely absent in lateral and posterior thalamic neurons of both cases (A1, B2, right figure; example of score 0). While the pontine tegmentum is mildy (D2; example of score +) and moderately (C1) affected in case 5 and case 2, respectively, neurons of n. propii of basis pontis show extensive Tau-pathology (D1; example of score +++), which is not observed in case 5 (C2). In contrast, prominent pathology in n. ambiguus is detected in case 5 (F2; example of score +++), and less in case 2 (E1) and to a lesser extent in magnocellular nuclei of formatio reticularis in both cases (F1, E2).

The autopsy of the two patients showed a neuronal tauopathy with predominant involvement of hypothalamus, prehypothalamic region, and tegmentum of brainstem including laterodorsal tegmental area, periaqueductal gray matter, the region of the pedunculopontine nucleus, magnocellular nuclei, and nucleus ambiguus (Table 3, FIG. 6). The Tau aggregates were exclusively neuronal, in form of pre-tangles, tangles and neuropil threads, with presence of 3-repeat and 4-repeat tau isoforms in patient 5 and predominance of 4-repeat tau isoforms in patient 2. Neurofibrillary pathology showed strong immunoreactivity for phospho-specific anti-tau antibodies Thr181, Ser262, Ser396, Ser422 (not shown). There were no tau-positive grains and no glial tau pathology, neither in astrocytes (tufted or thorn shaped astrocytes, bush-like or peculiar astrocytes or astrocytic plaques), nor in oligodendrocytes (coiled bodies, globular glial inclusions). No inflammatory infiltrates or concomitant abnormal protein deposits of beta-amyloid, alpha-synuclein, and TDP43 were detected. IgLON5 immunoreactivity was not reduced in the affected brainstem regions of patient 5 compared with those of a patient with Alzheimer disease used as control.

TABLE 1

Clinical features, treatment and outcome.

| Patient Sex/age at onset | Presenting symptoms (onset) | Disease duration (course) | Sleep problems | Gait | Bulbar Symptoms | Cognitive and psychiatric problems | Other symptoms | Treatment and outcome |
| --- | --- | --- | --- | --- | --- | --- | --- | --- |
| Patient 1 M/59 | Sleep problems (chronic) | 4 years (insidious) | Sleep movements and behaviors.* Stridor with OSA. Fragmented sleep. Occasional confusional awakenings.** Intermittent intense EDS | Normal | Right VC paresis | Mild memory and attention complaints. Apathy, low mood | Akathisia. Hypersalivation. Episodes of intense perspiration. | 3 cycles of iv steroids Ig, Cy No change |
| Patient 2 M/53 | Sleep problems (chronic) | 6 years (insidious/ fluctuating) | Sleep movements and behaviors.* Stridor with OSA. Fragmented sleep. Occasional confusional awakenings.** Nocturnal enuresis. Mild EDS | Normal | Mild dysphagia | Mild memory and attention complaints. Apathy, low mood | Akathisia | 3 cycles of iv steroids Ig, Cy No change Sudden death while asleep |
| Patient 3 M/52 | Sleep problems (subacute) | 5 years (insidious/ fluctuating) | Sleep movements and behaviors.* Stridor with OSA. Intense episodic EDS | Mild unsteadiness infrequent falls | Mild dysphagia and dysarthria. Bilateral VC paresis | Mild memory and attention complaints. Apathy, low mood | Akathisia Chorea | 3 cycles of iv steroids Ig, Cy No change |
| Patient 4 F/69 | Sleep problems (subacute) | 2 years (progressive) | Sleep movements. Loud "snoring" with OSA. Fragmented steep. Nocturnal confusional awakenings. Moderate EDS | No | Dysarthria. Episodes of central hypo-ventilation | Memory complaints Anxiety | Chorea. Syncopes with hypotension and bradycardia. Mild vertical gaze palsy | Iv steroids. No change Sudden death |
| Patient 5 F/76 | Gait instability with falls (subacute) | 6 months (rapidly progressive) | Sleep movements and behaviors* Stridor with OSA | Gait failure with severe postural instability | Dysphagia. Bilateral VC paresis. Central hypo-ventilation | Depressed mood | Mild oculomotor dysfunction with saccadic intrusions on pursuit | Iv/oral steroids No change Sudden death while asleep |
| Patient 6 F/65 | Gait difficulties (subacute) | 2 months (rapidly progressive) | Frequent sleep movements and behaviors. Loud "snoring" with OSA. Fragmented sleep | Gait failure with severe postural instability | Dysphagia. Mandibular spasms. Central hypo-ventilation | Long history of severe chronic depression | Bilateral horizontal nystagmus. Limba taxia. | Iv steroids, Ig, and rituximab Improved.*** Sudden death during daytime |
| Patient 7 F/59 | Gait instability with falls (chronic) | 12 years (slowly progressive) | Frequent sleep movements and behaviors. Loud "snoring". Mild EDS | Cerebellar ataxia. Severe postural instability | Dysphagia Dysarthria | Mental slowness with memory and attention difficulties Depressed mood | Chorea Bradykinesia Limb ataxia | Iv/oral steroids; rituximab No change Sudden death during daytime |
| Patient 8 F/58 | Gait instability with falls (chronic) | 5 years (slowly progressive) | Frequent sleep movements and behaviors. Stridor with OSA. Fragmented sleep. | Cerebellar ataxia | Dysphagia Dysarthria Central hypo-ventilation | Mild memory and attention complaints Depressed mood | Chorea Vertical/ horizontal nystagmus with saccadic intrusions Limb dysmetria | Iv Ig No change Dead from central hypoventilation |

Cy: cyclophosphamide;
EDS: Excessive daytime sleepiness;
Ig: immunoglobulins;
OSA: sleep obstructive apnea;
VC: Vocal cord.
*Video-polysomnography demonstrated a NREM and REM sleep parasomnia as the underlying substrate for the abnormal sleep movements and behaviors.
**Confusional awakening related to the anticholinergic effect of tricyclic antidepressants.
***Patient initially improved and could be discharged but she made a sudden death 2 days later

TABLE 2

Polysomnographic characteristics

1. Total sleep time is moderately reduced.
2. A distinctive temporal sequence of sleep stages and behaviours occurs, from most abnormal at the beginning of the night, to more normal at the end.
3. Rapid periodic leg movements during wakefulnes are often present, and they continue after sleep onset.
4. Initiation of sleep and re-entering sleep after awakening is abnormal with undifferentiated NREM sleep or poorly structured N2 sleep stage with frequent vocalizations, stereotyped repetitive upper limb movements and/or finalistic behaviors.
5. Normal N1 sleep stage is absent. Normal well-structured N2 sleep stage is infrequent or absent. Diffuse delta activity, typical of normal N3 sleep stage is present and always associated with frequent spindles.
6. REM sleep is present but only in the form of RBD
7. Sleep breathing disorder characterized by stridor and obstructive sleep apneas RBD: REM sleep behavior disorder

TABLE 3

Topographical distribution of neuronal loss and tau pathology

| Brain region | Patient 2 (table1) neuronal loss | Patient 2 (table1) tau | Patient 5 (table 1) neuronal loss | Patient 5 (table 1) tau |
|---|---|---|---|---|
| Neocortex | 0 | 0 | 0 | 0 |
| Hippocampus CA1, CA4 | + | ++ | 0 | + |
| Hippocampus CA2 | 0 | +++ | 0 | 0* |
| Dentate gyrus | 0 | ++ | 0 | 0* |
| Entorhinal cortex | + | ++ | 0 | + |
| Amygdala | 0 | 0* | 0 | + |
| Striatum | 0 | 0 | 0 | 0* |
| Pallidum, external | 0 | 0* | 0 | + |
| Pallidum, internal | 0 | + | 0 | ++ |
| N. basalis Meynert | + | ++ | 0 | + |
| Substantia innominata | + | ++ | + | ++ |
| Septal nuclei | + | ++ | 0 | + |
| Diagonal band | + | ++ | + | ++ |
| Preoptic area | + | ++ | + | ++ |
| Zona incerta | 0 | 0* | ++ | ++ |
| Subthalamic nucleus | 0 | 0* | + | + |
| Thalamus | | | | |
| Anterior | + | ++ | 0 | 0* |
| Dorsomedial | + | ++ | + | + |
| Posterolateral | 0 | 0 | 0 | 0 |
| Pulvinar | 0 | 0 | 0 | 0 |
| Hypothalamus | | | | |
| N. paraventricularis | + | + | 0 | + |
| N. supraopticus | + | + | 0 | + |
| N. ventromedialis | + | +++ | + | ++ |
| N. tuberales | + | ++ | + | ++ |
| N. posterior | + | ++ | + | ++ |
| Corpus mamillare | 0 | 0* | 0 | 0* |
| Brainstem/cerebellum | | | | |
| N. Laterodorsal tegmental | + | ++ | + | +++ |
| N. pedunculopontine | + | ++ | + | +++ |
| Periaquaeductal grey | ++ | + | + | ++ |
| Substantia nigra | 0 | 0* | 0 | 0* |
| Locus coeruleus | 0 | + | 0 | + |
| Central raphe (pons) | + | +++ | + | + |
| N. propii basis pontis | 0 | +++ | 0 | 0 |
| Dorsal n. vagal nerve | + | + | + | + |
| N. ambiguus | + | ++ | +++ | +++ |
| N. magnocellularis | + | ++ | ++ | +++ |
| Inferior olives | 0 | 0* | 0 | 0* |
| Cortex Cerebellum | 0 | ++ | 0 | 0 |
| Dentate nucleus | 0 | 0* | 0 | 0* |
| Cervical spinal cord | 0 | 0* | + | +++ |

Scores:
0 = absent (e.g. FIG. 5D1 for tau immunoreactivity), + = mild (e.g. FIG. 5A1), ++ = moderate (e.g. Fig. D2) and +++ = severe (e.g. FIG. 5C2, E1).
0* = isolated neuropil threads at 200x or 400x magnification.

The invention claimed is:

1. A method of detecting an autoantibody to IgLON5 or a fragment thereof in a subject, the method comprising:
   contacting a bodily fluid sample isolated from a subject with a polypeptide comprising IgLON5 or an IgLON5 fragment; and
   detecting the presence or absence of an autoantibody to IgLON5 in a complex with the polypeptide,
   wherein the IgLON5 comprises an amino acid sequence SEQ ID NO:1 or SEQ ID NO:12, and
   wherein the IgLON5 fragment comprises an amino acid sequence selected from a group of SEQ ID NO:2, SEQ ID NO:3, SEQ ID NO:4, SEQ ID NO:5; SEQ ID NO:6, SEQ ID NO:7, SEQ ID NO:8, SEQ ID NO:9, SEQ ID NO:10, and SEQ ID NO:11.

2. The method of claim 1, wherein the polypeptide is immobilized on a solid carrier.

3. The method of claim 1, wherein the detecting the presence or absence of the autoantibody to IgLON5 in a complex with the polypeptide comprises the use of a tagged or labeled secondary antibody.

4. The method of claim 1, wherein the polypeptide is provided in the form of a cell comprising a nucleic acid encoding the polypeptide or in the form of a tissue comprising the polypeptide.

* * * * *